United States Patent [19]

Wick et al.

[11] Patent Number: 4,690,931
[45] Date of Patent: Sep. 1, 1987

[54] THERAPEUTICALLY USEFUL 1-PHENYL-2-PIPERIDINOALKANOL DERIVATIVES

[75] Inventors: Alexander Wick, Paris; Jonathan Frost, Wissous; Bernard Gaudilliere, Nanterre; Jean Bertin, Clamart; Regis Dupont, Villebon sur Yvette; Jean Rousseau, Bourg la Reine, all of France

[73] Assignee: Synthelabo, Paris, France

[21] Appl. No.: 773,926

[22] Filed: Sep. 9, 1985

Related U.S. Application Data

[63] Continuation of Ser. No. 540,648, Oct. 11, 1983, abandoned.

[30] Foreign Application Priority Data

Oct. 13, 1982 [FR] France .................. 82 17187

[51] Int. Cl.$^4$ .................. C07D 211/18; A61K 31/445
[52] U.S. Cl. ...................................... 514/317; 546/240
[58] Field of Search ......................... 546/240; 514/317

[56] References Cited

U.S. PATENT DOCUMENTS

| | | | |
|---|---|---|---|
| 3,509,164 | 4/1970 | Carron et al. | 546/214 |
| 3,867,455 | 2/1975 | Atkinson et al. | 564/356 |
| 3,870,715 | 3/1975 | Hansl | 564/356 |
| 3,954,871 | 5/1976 | Buu-Hoi et al. | 564/356 |
| 4,011,258 | 3/1977 | Wetterlin et al. | 564/356 |
| 4,018,825 | 4/1977 | Schwender et al. | 564/356 |
| 4,021,485 | 5/1977 | Schromm et al. | 564/356 |
| 4,228,187 | 10/1980 | Lambelin et al. | 564/355 |
| 4,408,074 | 10/1983 | Signorini et al. | 564/356 |
| 4,430,334 | 2/1984 | Wick et al. | 546/237 |

OTHER PUBLICATIONS

Yasunobu Sato et al., Sankyo Kenkyusho Nempo, Ann. Sankyo Res. Lab., vol. 23, (1971), pp. 104–116.
C. Carron et al., Arzneim.-Forsch., vol. 21(12), (1971), pp. 1992–1998.

Derwent Abstract No. 46184T-B, abstracting FR-2105119-Q.
21CA 79:78372y; 81:152130c; 99:194509k.

Primary Examiner—Norma S. Milestone
Attorney, Agent, or Firm—Wegner & Bretschneider

[57] ABSTRACT

Compounds of the formula:

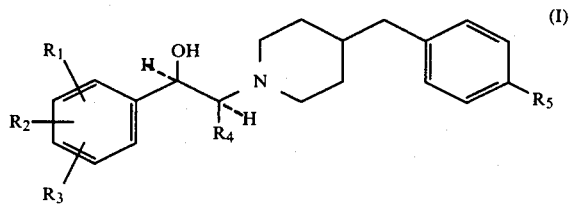

wherein
$R_1$ is hydrogen, halogen, trifluoromethyl, alkyl, hydroxyl, alkyoxy, benzyloxy, alkanoyloxy, or benzoyloxy, or when $R_2$ is hydroxyl or methoxy in the 4-position and $R_3$ is hydrogen, $R_1$ may also represent hydroxymethyl carbamoyl or alkoxycarbonyl,
$R_2$ is hydrogen, halogen, alkyl, hydroxyl, or alkoxy,
$R_3$ is hydrogen or alkyl,
$R_4$ is alkyl (in which case the compounds are ($\pm$)-erythro) or when $R_3$ represents hydrogen, $R_4$ may also be hydrogen, and $R_5$ is hydrogen, halogen, alkyl, alkoxy, or three methoxy groups in the 3-, 4- and 5-positions and pharmaceutically acceptable acid addition salts thereof, with the exclusion of compounds wherein:
(a) one of $R_1$ and $R_2$ is in the 4-position and is hydroxyl, alkoxy or benzyloxy, the other is in the 3-position and is hydrogen, hydroxyl, alkoxy or benzyloxy, and $R_3$ and $R_5$ are hydrogen and wherein:
(b) $R_1$ is in the 4-position and is halogen, $R_4$ is methyl and $R_2$, $R_3$ and $R_5$ are hydrogen, are useful as medicaments.

3 Claims, No Drawings

THERAPEUTICALLY USEFUL 1-PHENYL-2-PIPERIDINOALKANOL DERIVATIVES

This application is a continuation of Ser. No. 540,648, filed Oct. 11, 1983, now abandoned.

The present invention relates to new therapeutically useful 1-phenyl-2-piperidinoalkanol derivatives, to processes for their preparation and to pharmaceutical compositions containing them.

The compounds of the present invention are those of the general formula:

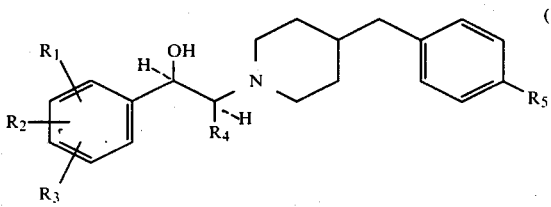

wherein
$R_1$ represents a hydrogen atom, a halogen atom, a trifluoromethyl group, an alkyl group having from 1 to 4 carbon atoms, a hydroxyl group, an alkoxy group having from 1 to 4 carbon atoms, a benzyloxy group, an alkanoyloxy group having from 1 to 16 carbon atoms or a benzoyloxy group, or, when $R_2$ represents a hydroxyl or methoxy group in the 4-position and $R_3$ represents a hydrogen atom, $R_1$ may also represent a hydroxymethyl group, a carbamoyl group or an alkoxycarbonyl group having from 1 to 4 carbon atoms in the alkoxy part, $R_2$ represents a hydrogen atom, a halogen atom, an alkyl group having from 1 to 4 carbon atoms, a hydroxyl group or an alkoxy group having from 1 to 4 carbon atoms, $R_3$ represents a hydrogen atom or an alkyl group having from 1 to 4 carbon atoms, $R_4$ represents an alkyl group having from 1 to 4 carbon atoms, in which case the compounds are in the (±)-erythro form, or, when $R_3$ represents a hydrogen atom, $R_4$ may also represent a hydrogen atom, and $R_5$ represents a hydrogen atom, a halogen atom, an alkyl group having from 1 to 4 carbon atoms, an alkoxy group having from 1 to 4 carbon atoms or a set of three methoxy groups in the 3-, 4- and 5-positions of the benzyl radical, and pharmaceutically acceptable acid addition salts thereof, with the exclusion of the compounds of general formula (I)
wherein:
(a) one of the substituents $R_1$ and $R_2$ is in the 4-position and represents a hydroxyl, alkoxy or benzyloxy group, the other is in the 3-position and represents a hydrogen atom or a hydroxyl, alkoxy or benzyloxy group, and $R_3$ and $R_5$ each represent a hydrogen atom, and wherein
(b) $R_1$ is in the 4-position and represents a halogen atom, $R_4$ represents a methyl group and $R_2$, $R_3$ and $R_5$ each represent a hydrogen atom.

Compounds of the general formula (I) wherein $R_1$ represents a hydroxyl group or a halogen atom in the 4-position, $R_2$, $R_3$ and $R_5$ each represent a hydrogen atom and $R_4$ represents a methyl group are described in French Pat. No. 5,733M and in European Patent Application No. 63,084.

Compounds of the general formula (I) wherein $R_1$ and $R_2$ represent one or two optionally etherified hydroxyl groups are described in French Pat. No. 2,163,358.

The preferred compounds of the invention are those of general formula (I)
wherein:
$R_1$ represents a hydrogen atom, a halogen atom, a trifluoromethyl group, a methyl group, a hydroxyl group or a methoxy group,
$R_2$ represents a hydrogen atom, a halogen atom, a methyl group, a hydroxyl group or a methoxy group,
$R_3$ represents a hydrogen atom or a methyl group,
$R_4$ represents a hydrogen atom or a methyl group and
$R_5$ represents a hydrogen atom, a halogen atom or a methyl group, a methoxy group or a set of three methoxy groups in the 3-, 4- and 5-positions; in this category of compounds, preference is given in particular to those of general formula (I) wherein $R_1$ represents a halogen, $R_2$ and $R_3$ represent hydrogen, $R_4$ represents hydrogen or methyl and $R_5$ represents hydrogen or a halogen.

Other preferred compounds of the invention are those of general formula (I)
wherein:
$R_1$ represents a hydroxymethyl, methoxycarbonyl, ethoxycarbonyl or carbamoyl group
$R_2$ represents a hydroxy group in the 4-position,
$R_3$ represents a hydrogen atom,
$R_4$ represents a methyl group and
$R_5$ represents a hydrogen atom.

The compounds of the formula (I) can be prepared according to the following reaction scheme:

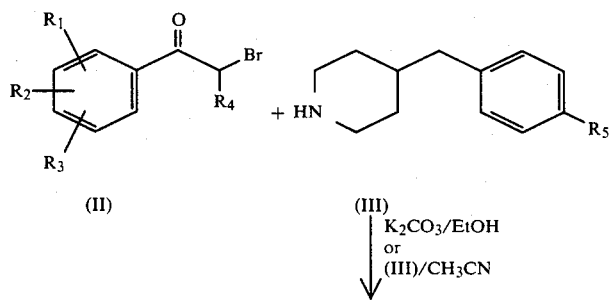

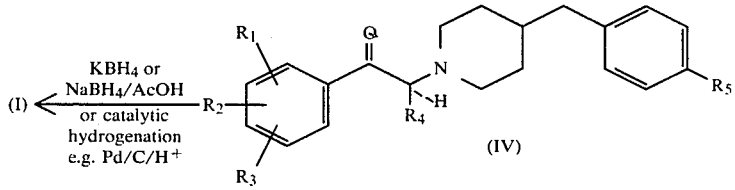

Thus, the present invention provides a process for the preparation of the compounds of general formula (I) which comprises the reaction of a ketone of general formula (II) with a benzylpiperidine of general formula (III) to obtain a ketone of general formula (IV), optional conversion of one or more of the substituents $R_1$, $R_2$ and $R_3$ into other substituents within the definition of $R_1$, $R_2$ and $R_3$, reduction of the ketone of general formula (IV) to obtain a compound of general formula I, and optional conversion of one or more of the substituents $R_1$, $R_2$ and $R_3$ into other substituents within the definition of $R_1$, $R_2$ and $R_3$.

The acetophenones and propiophenones of the formula (II) are commercially available, at least in their form which is not brominated in the α-position; otherwise, they can be prepared from known products by known methods.

Thus, for example, an appropriately substituted benzoic acid can be used to prepare the corresponding acid chloride and this can be reacted with ethylmagnesium bromide or diethylcadmium.

Alternatively, a diphenylcadmium compound can be prepared from an appropriately substituted bromobenzene and reacted with propionyl chloride.

It is also possible to prepare the propiophenones from an ethylmagnesium compound and a substituted benzonitrile or benzamide. In the case where one of the substituents $R_1$, $R_2$ and $R_3$ is a hydroxyl group, this can be esterified with propionic acid and the ester obtained can be subjected to a Fries rearrangement.

The unbrominated propiophenones of general formula II in which Br is replaced by H can be brominated by known methods, for example directly with bromine, in solution in a suitable solvent such as chloroform, or in a mixture of dioxane and diethyl ether, by a method described in Japanese Patent Application No. 56/43,266. It is also possible to use a selective brominating agent such as pyrrolidinone hydrotribromide of the formula:

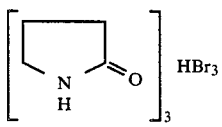

with tetrahydrofuran as the solvent.

The description of the above processes applies to propiophenones (of general formula II wherein $R_4=CH_3$). It will be appreciated by those skilled in the art that such processes can be adapted for the preparation of the corresponding acetophenones (of general formula II wherein $R_4=H$) and of the corresponding alkanones of general formula II wherein $R_4$ represents an alkyl group of from 2 to 4 carbon atoms.

The benzylpiperidines of the general formula (III) are also commercially available or, if not, can be prepared by knwon methods.

Thus, it is possible to carry out a Friedel-Crafts reaction of isonicotinoyl chloride and a benzene substituted by $R_5$, to reduce the ketone obtained and then to hydrogenate the heterocyclic ring. It is also possible to start from the already hydrogenated acid, namely isonipecotic acid, to acylate it on the nitrogen before preparing the chloride, then to react the latter with a benzene substituted by $R_5$, to form the hydrazone of the ketone obtained and, finally to treat the latter with sodium hydroxide in the presence of ethylene glycol in order simultaneously to decompose the hydrazone and free the heterocyclic nitrogen.

The reaction of the compounds of the general formulae II and III is generally carried out in the presence of a weak inorganic base such as sodium carbonate or potassium carbonate, in a solvent such as an alcohol, for example ethanol, or such as a ketone, for example methyl ethyl ketone, or alternatively in a proportion of two mol of benzylpiperidine of the general formula III per mol of propiophenone of the general formula II, in acetonitrile. In this case, it is the excess benzylpiperidine which fixes the hydrobromic acid released by the reaction.

The reduction of the ketone of the general formula IV is also carried out by known methods, for example either with sodium borohydride or potassium borohydride in an acid medium, or by catalytic hydrogenation (using, for example palladium on charcoal or platinum oxide as catalyst) when the symbols $R_1$, $R_2$, $R_3$ and $R_5$ do not denote halogen atoms.

The compounds of the general formula I can themselves be converted by known methods to other compounds of the general formula I; for example, a hydroxyl group can be converted to an alkoxy group by alkylation by known methods. The substituents $R_1$, $R_2$ and $R_3$ can also be modified in the ketone of the general formula IV, that is to say before the latter is reduced. Thus, for example, it is possible to esterify a hydroxyl group, transesterify an alkoxycarbonyl group or reduce an alkoxycarbonyl group to a hydroxymethyl group (after having protected the ketone group in the last case) before carrying out the final reduction step.

Pharmaceutically-acceptable acid addition salts of the compounds of general formula (I), e.g. methanesulphonates, mandelates, fumarates, maleates, malonates, citrates, hydrochlorides, hydrobromides and hydroiodides, may be obtained by known methods, for example by treatment of the compound of general formula I with the appropriate acid in a solvent medium, e.g. an alkanol or ether, or mixtures thereof.

By the term 'known methods' as used in this specification is meant methods heretofore used or described in the literature.

The following Examples illustrate the preparation of compounds of the invention. Examples 1 to 22 relate to the preparation of ketones of general formula II, Examples 23 to 25 relate to the benzylpiperidines of general formula III and Examples 26 to 49 relate to compounds of general formula I.

The elementary analyses and the IR and NMR spectra of the compounds prepared confirm their structures.

EXAMPLES OF THE PREPARATION OF KETONES OF THE FORMULA II

EXAMPLE 1

2-Bromopropiophenone

A pinch of aluminium chloride ground beforehand in a mortar is added to 13.4 g (0.1 mol) of propiophenone in 100 ml of anhydrous chloroform, and a solution of 5 ml (0.1 mol) of bromine in 20 ml of chloroform is then added dropwise, with stirring. The mixture decolourises instantaneously. It is cooled in an ice bath and then stirred overnight to drive off the hydrobromic acid formed. The catalyst is filtered off and the solvent is driven off from the filtrate. 22 g of an oil remain, which is used as such in a subsequent step.

EXAMPLE 2

2-Bromo-4'-hydroxypropiophenone 15 g (0.12 mol) of p-hydroxypropiophenone are added to a mixture of 16 ml of dioxane and 60 ml of diethyl ether. The suspension is heated to 30° C. and 22.4 g (0.14 mol) of bromine are added dropwise. Stirring is continued for 1 hour at ambient temperature.

40 ml of water and 40 ml of diethyl ether are then added, the organic phase is decanted, washed with water and dried over magnesium sulphate and the solvent is driven off to give a crude product. Recrystallization of the crude product from toluene gives 18 g of fine lilac crystals which melt at 95°-97° C.

EXAMPLE 3

2-Bromo-4'-chloropropiophenone

A solution of 15.9 g (0.1 mol) of bromine in 20 ml of chloroform is added dropwise to a solution of 16.8 g (0.1 mol) of 4'-chloropropiophenone in 100 ml of chloroform, in the presence of a small amount of aluminium chloride, and the mixture is stirred overnight. After filtration and evaporation of the filtrate, the crystalline residue is washed with petroleum ether. When dry, it melts at 75° C.

EXAMPLE 4

2-Bromo-3'-chloropropiophenone 4.86 g (0.2 mol) of magnesium turnings, 30 ml of dry diethyl ether and a grain of iodine are placed in a one liter three-necked round-bottomed flask equipped with a condenser, a calcium chloride drying tube, a pressure equalizing funnel and a magnetic stirrer; the flask is purged with nitrogen, and 21.8 g (0.2 mol) of ethyl bromide in 30 ml of dry diethyl ether are then added. The mixture is then heated under reflux for one hour and left to cool. At ambient temperature, 16.51 g (0.12 mol) of 3-chlorobenzonitrile in 70 ml of dry diethyl ether are then added. A copious precipitate forms. The mixture is stirred overnight at ambient temperature and then cooled in an ice bath and hydrolysed by slowly adding 50 ml of water and then about 100 ml of 6N hydrochloric acid until the pH is acid. The mixture is stirred for one and a half hours and then extracted with ethyl acetate. The organic extract is then washed twice with water, dried and concentrated on a rotary evaporator. This gives 26 g of an orange oil, which is concentrated in vacuo to give about 18.2 g of ochre crystals of 3'-chloropropiophenone melting at about 40° C.

18 g (0.1 mol) of these crystals, together with 100 ml of chloroform and a pinch of aluminium chloride, are placed in a 250 ml conical flask equipped with a pressure equalizing funnel, a calcium chloride drying tube and a magnetic stirrer, and a solution of 5.47 ml (0.1 mol) of bromine in 15 ml of chloroform is then added slowly at ambient temperature. Stirring is continued for one hour, the mixture is then filtered on a glass frit and the filtrate is concentrated on a rotary evaporator to give an orange oil, which is taken up in 100 ml of chloroform and washed with 100 ml of 5% aqueous sodium bicarbonate solution and then with 100 ml of 5% sodium thiosulphate solution. After drying over magnesium sulphate and concentration on a rotary evaporator, 29.8 g of an orange oil remain, which can be used as such in a subsequent step.

EXAMPLE 5

2-Bromo-2'-chloropropiophenone

The procedure of Example 4 is used, except that 16.51 g of 2-chlorobenzonitrile are used instead of 3-chlorobenzonitrile. The 2'-chloropropiophenone obtained after extraction with ethyl acetate is a brown oil which distils under a pressure of about 2.6 kPa and at a temperature of 120° C. About 11.0 g thereof are collected and subjected to bromination as described in Example 4. 26.3 g of a yellow oil are finally obtained, which is used as such in a subsequent step.

EXAMPLE 6

2-Bromo-3'-fluoropropiophenone

The procedure of Example 4 is used, except that 3-fluorobenzonitrile is used instead of 3-chlorobenzonitrile. 3'-fluoropropiophenone is a greenish oil. 2-bromo-3'-fluoropropiophenone is a yellow oil, which is used as such in a subsequent step.

EXAMPLE 7

2-Bromo-2'-fluoropropiophenone

The procedure of Example 4 is used, except that 2-fluorobenzonitrile is used instead of 3-chlorobenzonitrile. 2'-fluoropropiophenone and 2-bromo-2'-fluoropropiophenone are colourless oils.

EXAMPLE 8

2-Bromo-4'-trifluoromethylpropiophenone 43.5 g (0.229 mol) of 4-trifluoromethylbenzoic acid are introduced in portions into a 500 ml three-necked flask equipped with a magnetic stirrer and containing 150 ml of thionyl chloride, and the mixture is then heated gradually to about 70° C. After 6 hours at this temperature, the mixture is left to stand for 20 hours and the excess thionyl chloride is then driven off in vacuo. The oily residue is then distilled under a pressure of 130 to 650 Pa. A colourless fraction consisting of 42.1 g of 4-trifluoromethylbenzoyl chloride is collected at between 36° and 40° C.

A crystal of iodine is added to a suspension of 9.6 g of magnesium turnings, previously ground in a mortar, in 120 ml of dry diethyl ether, and a solution of 43.6 g (0.4 mol) of ethyl bromide in 80 ml of dry diethyl ether is then added slowly, the mixture being cooled at the same time in order to limit the reflux of the solvent. The mixture is then heated under reflux for half an hour and cooled to 5° C. and 36.7 g of cadmium chloride, dried beforehand, are added in portions. The resulting reaction is very exothermic; the temperature of the mixture is kept below 10° C. A further 100 ml of diethyl ether are added in order to make the mixture more fluid. The mixture is heated under reflux for 40 minutes and left to stand overnight at ambient temperature. The diethyl ether is then evaporated off in vacuo, the pasty residue is taken up in 140 ml of dry benzene, the mixture obtained is cooled to between 5° and 10° C. and a solution of 41.7 g (0.2 mol) of the previously prepared 4-trifluoromethylbenzoyl chloride in 60 ml of dry benzene is added slowly so as to keep the temperature below 10° C. After this addition, the mixture is allowed to return to ambient temperature, stirring being continued for one hour in order to homogenize it, and then heated for two hours under reflux. The mixture is cooled in an ice bath to 10° C. and then poured into an ice saturated solution of sodium chloride, with stirring.

The precipitate which forms is filtered off and washed with diethyl ether. The phases of the filtrate are separated by decantation and the milky aqueous phase is extracted with diethyl ether. The organic phases are combined, extracted with dilute sodium hydroxide solution, washed, dried over sodium sulphate and concentrated in vacuo. After distillation under a vacuum of about 6.5 Pa at between 50° and 56° C. and recrystallization from petroleum ether, 14.4 g of white crystals of 4'-trifluoromethylpropiophenone melting at 36°-37° C. are obtained. 12.25 g of this compound are dissolved in 100 ml of methylene chloride, and 3.25 ml of bromine are added dropwise, with vigorous stirring; the bromine is immediately decolourised. The dropping funnel is then rinsed with 20 ml of methylene chloride and the mixture is stirred at ambient temperature for one and a half hours and then left to stand overnight. The organic phase is washed with water until the pH of the washings is neutral, dried and evaporated to dryness. The oily residue obtained crystallises in the refrigerator to form 16.5 g of colourless crystals.

EXAMPLE 9

2-Bromo-3'-trifluoromethylpropiophenone

The procedure of Example 4 is used, except that 3-trifluoromethylbenzonitrile is used instead of 3-chlorobenzonitrile.

EXAMPLE 10

2-Bromo-2'-trifluoromethylpropiophenone 4.86 g (0.2 mol) of magnesium turnings, 50 ml of dry diethyl ether and a grain of iodine are placed in the apparatus described in Example 4, and 43.88 g (0.195 mol) of 1-bromo-2-trifluoromethylbenzene are then added slowly at ambient temperature so as to cause gentle reflux of the solvent. Stirring is continued for one hour and 18.35 g (0.1 mol) of cadmium chloride are then added. After a quarter of an hour, when the transmetallisation is complete, the mixture is concentrated on a rotary evaporator, toluene is added and the mixture is concentrated again. These three operations are repeated in order to remove the maximum amount of diethyl ether.

27.75 g (0.3 mol) of propionyl chloride in 25 ml of toluene are then added at ambient temperature, after which the mixture is heated under reflux for two hours and left to cool under a nitrogen atmosphere overnight. The mixture is then hydrolysed with 200 ml of water and 6N hydrochloric acid until a pH of 2 to 3 is obtained. The mixture is extracted with ethyl acetate (5×200 ml) and the organic phases are combined and washed with water until the pH of the washings is neutral. After drying over magnesium sulphate and concentration on a rotary evaporator, 34.4 g of a crude oil are collected, which is then distilled under a pressure of about 3.3 kPa. At 100° C., a fraction consisting of 14.15 g of an oil passes over, which becomes bluish after a few moments. Bromination as described in Example 4 gives a greenish oil, which is used as such in a subsequent step.

EXAMPLE 11

2-Bromo-2'-methylpropiophenone

A solution of 41.8 g of ethyl bromide in 50 ml of dry diethyl ether is added to a suspension of 10 g of magnesium in 150 ml of dry diethyl ether. After stirring for 8 hours, 35 g of cadmium chloride are added in small portions and the mixture is left to stand overnight.

25 g of 2-methylbenzoyl chloride and 150 ml of dry diethyl ether are placed in a 2 liter three-necked flask, the above mixture is introduced gradually and stirring is continued for 30 hours at ambient temperature. The mixture is then hydrolysed with water and dilute hydrochloric acid and the organic phase is separated off and washed with dilute sodium hydroxide solution and then with water. After drying over sodium sulphate and evaporation of the diethyl ether, an oil remains, which is subjected to bromination in 100 ml of chloroform by adding 6.5 ml of bromine diluted in 10 ml of chloroform. After stirring for one hour, the mixture is filtered and the filtrate is evaporated to leave 27 g of 2-bromo-2'-methylpropiophenone in the form of an oil.

EXAMPLE 12

2-Bromo-4'-methylpropiophenone 14.8 g (0.1 mol) of 4'-methylpropiophenone are introduced into 100 ml of chloroform, in the presence of a small amount of finely ground aluminium chloride, and a solution of 15.9 g (0.1 mol; 5 ml) of bromine, in 20 ml of chloroform is added dropwise whilst cooling with an ice bath. The mixture is left to react overnight at ambient temperature. It is then filtered, the solvent is evaporated off from the filtrate and the crystalline residue is washed with diethyl ether. 21.5 g of crystals are collected.

EXAMPLE 13

2-Bromo-3'-methyl-4'-hydroxypropiophenone 79.7 g (1.355 mol) of 2-hydroxy-toluene in 480 ml of toluene are placed, together with 55.3 g (0.70 mol; 56.3 ml) of pyridine, in a 1 liter three-necked round-bottomed flask equipped with a magnetic stirrer, a condenser with a calcium chloride drying tube, and a pressure equalizing funnel, and 64.75 g (0.70 mol; 60.8 ml) of propionyl chloride are then poured in slowly. A copious white precipitate forms. The mixture is then heated under reflux for one hour and left to cool and a further 8 ml (0.1 mol) of pyridine are then added, followed by the dropwise addition of 6.1 ml (0.1 mol) of propionyl chloride. the mixture is heated under reflux for one hour, left to cool and filtered on a glass frit to remove the pyridinium chloride, and an orange filtrate is collected, which is washed successively with 200 ml of 1N hydrochloric acid, 200 ml of 1N sodium hydroxide solution, 200 ml of water, 200 ml of 1N hydrochloric acid and water (2×150 ml). The organic phase neutralised in this way is then dried over sodium sulphate and concentrated on a rotary evaporator and then under a vane pump vacuum. 93.9 g of an orange-brownish oil finally remain.

Distillation of the oil under a pressure of 50 to 90 Pa at between 52° and 58° C. gives 72.2 g of colourless 2-methylphenylpropionate, which is to be subjected to a Fries rearrangement.

The propionate obtained is poured slowly into a 1 liter conical flask equipped with a magnetic stirrer, a condenser, a calcium chloride drying tube and a pressure equalizing funnel, under a nitrogen atmsophere, and containing 86.4 g (0.648 mol) of aluminium chloride, and the mixture is then heated at 50° C. for 3 hours. Hydrogen chloride is evolved and the mixture becomes a green paste. The mixture is left to stand for 48 hours and then hydrolysed with 200 ml of water and 100 ml of 10% hydrochloric acid. The mixture is extracted with toluene and concentration of the organic phases gives a yellowish-brown oil, which is subjected to steam distillation. The aqueous phase thus obtained is acidified with 6N hydrochloric acid to a pH of 2 to 3, a first extraction is carried out with 250 ml of toluene, the remaining aqueous phase is saturated with sodium chloride and a second extraction is carried out with 250 ml of toluene.

The two organic phases thus obtained are combined, dried, and the solvent evaporated off. 39.71 g of light brown crystals remain, which are recrystallized from a mixture of petroleum ether and ethyl acetate. 24.8 g of light grey crystals of 3'-methyl-4'-hydroxypropiophenone are finally collected, which give a single spot in thin layer chromatography and have a melting point of 86° C.

8.21 g (0.05 mol) of the crystals obtained are dissolved in a mixture of 6.6 ml of dioxane and 25 ml of diethyl ether, 9.58 g (0.06 mol; 3.07 ml) of bromine are added dropwise, the mixture is stirred overnight at ambient temperature, the precipitate which forms is filtered off and collected and the filtrate is evaporated to yield a solid residue. The precipitate and residue are combined to yield 14 g of bromine derivative, which is used as such in a subsequent step.

EXAMPLE 14

2-Bromo-3'-methyl-4'-methoxypropiophenone

The procedure of Example 13 is used, the bromination step being preceded by a step involving methylation of the hydroxyl group. In order to effect the methylation, a solution of 8.2 g (0.95 mol) of 3'-methyl-4'-hydroxypropiophenone is prepared in 20 ml of water containing 2 g (0.05 mol) of sodium hydroxide. This solution is cooled to below 10° C. and 4.7 ml (0.05 mol) of dimethyl sulphate are added dropwise. The mixture is stirred for half an hour at 100° C. It is then left to cool, the supernatant oil is extracted with toluene (2×50 ml), the extract is dried and the solvent is driven off. 9.2 g of a very mobile oil remain, which is subjected to bromination under the conditions described in Example 13. This gives a semicrystalline solid, which is used as such in a subsequent step.

EXAMPLE 15

2-Bromo-3',5'-dichloropropiophenone 3,5-Dichlorobenzoyl chloride is first prepared by heating 25 g of the free acid under reflux in 50 ml of thionyl chloride for 4 hours. The excess thionyl chloride is then evaporated off, toluene is added and evaporated off and this operation is repeated in order to remove all traces of thionyl chloride.

In a separate operation, 41.8 g of ethyl bromide diluted in 50 ml of dry diethyl ether are introduced into 150 ml of dry diethyl ether containing 10 g of magnesium, and the cadmium derivative is then prepared by adding 35 g of cadmium chloride and leaving the mixture to react overnight.

The acid chloride is diluted with dry diethyl ether, the cadmium derivative prepared as described above is added in small portions and the mixture is left to react overnight. It is then poured into iced water, the mixture obtained is acidified with 3N hydrochloric acid and left to separate, and the aqueous fraction is extracted with diethyl ether. The organic phases are washed with water and dried over sodium sulphate and the solvent is driven off. This gives 18.6 g of an oil, which is diluted with 70 ml of chloroform; 14.34 g (4.61 ml) of bromine diluted in 25 ml of chloroform are then added dropwise. The mixture is left to react for 2 hours, water is then added, the mixture is left to separate, the organic phase is washed with water and then dried and the chloroform is evaporated off. 20 g of a brown oil are collected, which is used as such in a subsequent step.

EXAMPLE 16

2-Bromo-2',4'-dichloropropiophenone 43 g of 2,4-dichlorobenzoyl chloride are introduced dropwise, under nitrogen, into a 500 ml three-necked flask containing 200 ml of concentrated aqueous ammonia solution (25%), cooled in an ice bath. A copious precipitate forms, which is filtered off after one hour and washed with water. After drying in a vacuum oven, 42 g of amide melting at 193° C. are collected. In a separate operation, ethyl magnesium iodide is prepared in 300 ml of dry diethyl ether from 19.8 g of magnesium and 88.9 g of ethyl iodide. 41.1 g of the previously prepared amide are then added in portions. The reaction is exothermic. After the addition has ended, the suspension obtained is heated under reflux for 4 hours, left to stand overnight, heated under reflux for a further 8 hours and left to stand overnight. The mixture is then poured into 1.5 liters of iced water and acidified with concentrated hydrochloric acid, which solubilizes the aqueous phase, and the mixture is then left to separate. The aqueous phase is extracted with diethyl ether, the extracts are washed with water and dried and the diethyl ether is driven off. An oily suspension remains, from which the unreacted amide is removed by filtration. The syrupy filtrate is diluted with chloroform, treated with decolourising charcoal and sodium sulphate and filtered. After evaporation, 39.8 g of a brown oil remain, which is subjected to bromination. For this purpose, it is diluted in 200 ml of chloroform, a crystal of aluminium chloride is added and 10 ml of bromine diluted in 40 ml of chloroform are added dropwise. To the stirred mixture aqueous sodium thiosulphate is added, the mixture is left to separate, the organic phase is washed with water and dried and the solvent is driven off. 51 g of a crude brown oil remain, which is used as such in a subsequent step.

EXAMPLE 17

2-Bromo-3',5'-dimethylpropiophenone 3,5-Dimethylbenzoyl chloride, and diethylcadmium, are prepared as described in Example 15. The organocadmium compound is then introduced into a 2 liter three-necked flask containing 26 g of the acid chloride and 200 ml of dry diethyl ether and the mixture is left to react for 48 hours. It is then poured onto crushed ice and acidified with 3N hydrochloric acid; the diethyl ether phase is separated off, washed with 6N sodium hydroxide solution and then with water, dried and evaporated. 26 g of an oil remain, half of which is diluted in 100 ml of chloroform; 4.2 ml of bromine diluted in 50 ml of chloroform are then added. After this addition, the mixture is stirred for 2 hours at ambient temperature, the solvent is evaporated off, the residue is taken up in 100 ml of chloroform and the solvent is evaporated off again. 21 g of an oil remain, which is used as such in a subsequent step.

EXAMPLE 18

2-Bromo-4'-hydroxy-3'-fluoropropiophenone 64.75 g (0.70 mol) of propionyl chloride are introduced slowly, at ambient temperature, into a round-bottomed flask equipped with a pressure equalizing funnel, a condenser with a calcium chloride drying tube, and a magnetic stirrer, and containing 400 ml of toluene, 60 g (0.54 mol) of 2-fluorophenol and 55.3 g (0.70 mol) of pyridine. After stirring for one hour, the white precipitate which forms is filtered off and the filtrate is washed with water until the pH of the washings is 7. After drying and evaporation of the solvent, 90 g of ester are collected in the form of an oil.

133.3 g (1 mol) of aluminium chloride are placed in a 1 liter conical flask equipped with a pressure equalizing funnel, a stirrer and a condenser with a calcium chloride drying tube, and 82 g of the above oil are poured in slowly.

The mixture is then heated at 165° C. for 2 hours. It is then hydrolysed with water followed by 6N hydrochloric acid and extracted with ethyl acetate; the extract is dried and filtered and the solvent is driven off. 70 g of oily black crystals remain, which are dissolved in hot cyclohexane. Cooling of the solution produces a light yellow precipitate. By repeating the recrystallization, 30 g of white crystals which melt at 101°–102° C. are finally collected. The crystals obtained are brominated under the conditions described in Example 13.

EXAMPLE 19

2-Bromo-4'-hydroxy-3'-methoxycarbonylpropiophenone 600 ml of 1,2-dichloroethane, 76 g (0.5 mol; 65 ml) of methyl salicylate and 50.9 g, (0.5 mol; 48 ml) of propionyl chloride are placed in a 2 liter three-necked flask equipped with a mechanical stirrer, a condenser and a thermometer. The mixture is cooled to 0° C. and 133 g (1 mol) of ground aluminium chloride are added in small amounts in such a way that the temperature remains below 15° C. The mixture is then stirred for a further 4 hours at ambient temperature and left to stand overnight. It is then poured into 2 liters of water and ice and the organic phase is separated off and washed with water, sodium bicarbonate solution and water again. After drying and evaporation, an oil is obtained, which is crystallised from hexane. 93 g of propiophenone as crystals melting at 62°–64° C. are collected.

To effect bromination of the propiophenone, 70 ml of diethyl ether, 17 ml of dioxane and 26 g of the previously obtained propiophenone are placed in a 250 ml conical flask equipped with a thermometer, a condenser and a dropping funnel. 7.4 ml of bromine are then added dropwise, the mixture being cooled in an ice bath. Stirring is continued for 4 hours, the mixture is then poured into iced water and the organic phase is decanted, washed with water (3×250 ml), dried over magnesium sulphate and evaporated to dryness. 30 g of a product are thus isolated, which is recrystallized from an 80/20 mixture of diisopropyl ether/toluene. 22 g of crystals which melt at 102° C. are finally collected.

EXAMPLE 20

2-Bromo-4'-hydroxy-3',5'-dimethylpropiophenone 92 g (1 mol) of propionyl chloride are added to 500 ml of toluene containing 61 g (0.5 mol) of 2,6-dimethylphenol, and 79 g of pyridine are then added dropwise, with stirring. The mixture is then heated under reflux for one hour, cooled, poured into 1 liter of water containing 3% of hydrochloric acid, and stirred, and the organic phase is left to separate out, separated off, washed with water, dried over sodium sulphate and evaporated. This gives 100 g of a very mobile oil, which is used as such for the subsequent rearrangement. For this purpose, it is dissolved in 300 ml of chlorobenzene and this solution is poured slowly onto 100 g of aluminium chloride. The mixture is then heated at 80° C. for 5 hours, with stirring, left to cool and poured slowly into a mixture of 850 ml of iced water and 100 ml of concentrated hydrochloric acid. The resulting mixture is stirred for half an hour in the ice bath and the precipitate is filtered off. It is washed, drained and dried. 41 g of the precipitate are collected.

17.8 g of the precipitate are dissolved in a mixture of 13.2 ml of dioxane and 50 ml of dry diethyl ether at 30° C., 6.1 ml of bromine are then added dropwise, the mixture is stirred overnight at ambient temperature and the solvents are evaporated off. The residue is used as such in a subsequent step.

EXAMPLE 21

2-Bromo-4'-methoxy-3',5'-dimethylpropiophenone

The procedure of Example 20 is used, the bromination step being preceded by a methylation step.

To carry out the methylation, 4.45 g of 4'-hydroxy-3',5'-dimethylpropiophenone are placed in a 50 ml round-bottomed flask together with 10 ml of water and 1 g of sodium hydroxide. The mixture is cooled to below 10° C. and 2.35 ml of dimethyl sulphate are added dropwise. The mixture is then heated in an oil bath at 100° C. for half an hour and left to stand overnight at ambient temperature. It is extracted with 20 ml of toluene, the mixture is left to separate, the organic phase is dried and evaporated and 4.2 g of a mobile oil are collected; the oil is diluted in a mixture of 4 ml of dioxane and 12 ml of diethyl ether; 1.13 ml of bromine are added dropwise, the mixture obtained is stirred for 1 hour at ambient temperature and left to stand overnight and the solvents are driven off. 5.9 g of an oil remain, which is used as such in a subsequent step.

EXAMPLE 22

2-Bromo-4'-ethylpropiophenone

A mixture of 100 g of 4-ethylbenzoic acid and 250 ml (153 g) of thionyl chloride is heated for 2 to 3 hours at 80° C., with stirring, until dissolution is complete. The solution is then left to cool, the excess thionyl chloride is evaporated off in vacuo and the liquid residue is distilled under about 13 Pa at 90° C. 95.2 g of the acid chloride are collected in the form of a colourless liquid.

Diethylcadmium is then prepared, as described in Example 8, from 63 g of ethyl bromide, 13.8 g of magnesium and 53 g of cadmium chloride. It is suspended in 400 ml of benzene, and a solution of 48.7 g of the previously prepared 4-ethylbenzoyl chloride diluted in 100 ml of benzene is then added dropwise, while cooling to below 10° C. After the addition, the mixture is stirred for one hour at ambient temperature and then for 2 hours at the reflux temperature. It is then cooled to 10° C. and poured onto a mixture of ice and salt, with stirring; the resulting mixture is filtered and the organic phase is separated from the filtrate, extracted twice with dilute sodium hydroxide solution, washed with water, dried over magnesium sulphate and evaporated. 48.4 g of an oily residue remain, which is distilled under a high vacuum (13 Pa). A fraction consisting of 35.6 g of virtually pure 4'-ethylpropiophenone passes over at between 65° and 80° C. In order to effect bromination of the propiophenone, 34.8 g thereof are dissolved in 1,000 ml of tetrahydrofuran, and 17.5 ml of pyrrolidinone and then 114 g of pyrrolidinone hydrotribromide are added. The mixture is heated under reflux, with stirring; it decolourises gradually and pyrrolidinone hydrobromide precipitates. The reaction is complete after one hour, the hydrobromide is filtered off and rinsed with ethyl acetate and the solvents are evaporated off from the filtrate. The partially crystalline, oily orange residue is taken up in a mixture of water and methylene chloride. The organic phase is separated off, washed twice with water, dried and evaporated in vacuo. The greenish oily residue is dissolved in toluene, pentane is added, a small greenish gummy fraction is filtered off on paper and the filtrate is evaporated. An oily residue remains, which is used as such in a subsequent step.

EXAMPLES OF THE PREPARATION OF BENZYLPIPERIDINES OF THE FORMULA III

EXAMPLE 23

4-(4-Methylbenzyl)-piperidine 123 g (1 mol) of isonicotinic acid are placed in a 1 liter round-bottomed flask equipped with a condenser and a calcium chloride drying tube, and 250 ml of thionyl chloride are added all at once, whilst cooling with an ice bath. The exothermic reaction lasts about ten minutes. The mixture is then heated under reflux on an oil bath for one and a half hours. The excess thionyl chloride is driven off and the crystalline residue is taken up in 100 ml of dry diethyl ether. The mixture is stirred and the white precipitate which forms is filtered off, washed again with 50 ml of diethyl ether and dried to yield 171 g of isonicotinoyl chloride in the form of the hydrochloride. 92 g (0.516 mole) of this are placed in a 2 liter three-necked flask equipped with a thermometer, a stirrer, a condenser and a calcium chloride drying tube, and 300 ml of anhydrous toluene are added. The mixture is cooled to 10° C., 262 g (1.96 mol) of ground aluminium chloride are added in small portions and the mixture is stirred for 2 hours at ambient temperature. The dark red solution is then transferred to a dropping funnel and added dropwise to 2.5 liters of iced water cooled with an ice bath. 800 ml of ethyl acetate are then added, followed by the addition of 1 liter of sodium carbonate solution (d=1.33), with cooling. This gives a solution from which the organic phase is decanted. The aqueous phase is extracted a further three times with 500 ml of ethyl acetate, the organic phases are combined, washed with water and dried and the solvent is evaporated off in vacuo in a water bath. The residue is triturated with 100 ml of ethanol, whilst cooling in an ice bath. It is isolated by filtration and dried to give 80 g of 4-(4-methylbenzoyl)-pyridine. 42.6 ml of hydrazine hydrate and 18.4 ml of water are then added, followed by 420 ml of ethylene glycol and then by 103.5 g of sodium hydroxide pellets. The mixture is heated under reflux for 2 hours and cooled and 1 liter of water is added. The supernatant oil is extracted with diethyl ether (4×250 ml). The ether phase is washed with water, dried and evaporated. This gives 72 g of 4-(4-methylbenzyl)-pyridine in the form of an oil which crystallises.

The crystals are dissolved in 200 ml of methanol, 2 g of 5% rhodium-on-charcoal are added and hydrogenation is carried out under 5 Mpa at about 70° C. for 8 hours. The catalyst is then filtered off and the solvent is evaporated off. 72 g of 4-(4-methylbenzyl)-piperidine, in the form of an oil, remain.

EXAMPLE 24

4-(4-Methoxybenzyl)-piperidine

The procedure of Example 23 is used, the toluene being replaced by anisole.

EXAMPLE 25

4-(4-Fluorobenzyl)-piperidine

A mixture of 300 g (2.32 mol) of isonipecotic acid and 1,200 ml of acetic anhydride is heated under reflux for 2 hours in a 4 liter reactor equipped with a mechanical stirrer, a condenser and a thermometer, and the mixture is left to stand overnight. 1 liter of diethyl ether is added to the mixture, which is starting to crystallise, the solid is filtered off and the cake is washed with diethyl ether (4×500 ml), drained and recrystallised from a 40/60 mixture of diisopropyl ether/isopropyl alcohol. 153 g are isolated in a first crop and 141 g in a second crop. The N-acetylisonipecotic acid obtained melts at 148° C.

141 g of this acid are introduced in small portions into a 4 liter round-bottomed flask equipped with a stirrer and containing 860 ml of thionyl chloride. The acid chloride precipitates. The mixture is stirred for a further 2 hours and 2 liters of petroleum ether are then added. The precipitate is filtered off, drained, washed three times with 500 ml of petroleum ether and dried in vacuo at 40° C. 140 g of this precipitate, which melts at about 122° C., are isolated. 198 g of aluminium chloride are added in small amounts to 350 ml of fluorobenzene placed in a 2 liter three-necked flask equipped with a stirrer and a condenser. 150 g of the previously prepared acid chloride are then added in small amounts to this suspension, the temperature being kept at about 20° C. by means of an ice bath. The mixture is then heated under reflux for one hour, after which it is poured into a mixture of 2 kg of ice and 1 liter of water. The product formed is extracted with methylene chloride. The organic phase is separated off, washed with water, dried and the solvent evaporated off. 170 g of N-acetyl-4-(4-fluorobenzoyl)-piperidine are collected in the form of an oil. 12.3 g of this are added to 5.375 ml of hydrazine hydrate and 2.3 ml of water, 150 ml of ethanol are added, the whole is heated under reflux for 8 hours and evaporated to dryness and the oily residue is taken up in diethyl ether. After stirring for 30 minutes, the hydrazone crystallises; it is isolated by filtration and drained. 10 g of the hydrazone are collected; after recrystallisation from a mixture of diisopropyl ether/ethanol, it melts at 145°–148° C.

A mixture of 26 g of the hydrazone, 27 g of sodium hydroxide and 200 ml of ethylene glycol is heated for 2 hours at 160° C. The mixture is then poured into 500 ml of iced water and extracted with chloroform. The organic phase is dried and evaporated, the residual oil is distilled and a 10.5 g fraction is collected, which distills at between 104° and 110° C. under 50 Pa. The hydrochloride is prepared by dissolving the orange oil obtained in acetone and adding a solution of hydrogen chloride in diethyl ether. After recrystallisation from a 98/2 mixture of acetone/ethanol, the hydrochloride melts at 158°–160° C.

EXAMPLES OF THE PREPARATION OF COMPOUNDS ACCORDING TO THE INVENTION

EXAMPLE 26

2-[4-(4-Methylbenzyl)-piperidino]-1-(4-hydroxyphenyl)-propanol and its hydrochloride 1. 2-[4-(4-Methylbenzyl)-piperidino]-4'-hydroxypropiophenone 7.57 g (0.04 mol) of 4-(4-methylbenzyl)-piperidine are introduced into 35 ml of ethanol, 9.15 g (0.04 mol) of 2-bromo-4'-hydroxypropiophenone and then 4.24 g (0.04 mol) of sodium carbonate are added and the mixture is heated under reflux for 2 hours. It is then cooled with an ice bath and 200 ml of iced water and 100 ml of toluene are added. The mixture is stirred and left to separate and the organic phase is separated off. The aqueous phase is extracted three times with 100 ml of toluene. The organic phases are combined, washed, dried and then evaporated. This gives 13 g of a pasty oil, which is purified by chromatography on silica using acetone as the eluant. 10 g of a pale oil are collected, which is used as such in the subsequent reduction.

2. 2-[4-(4-Methylbenzyl)-piperidino]-1-(4-hydroxyphenyl)-propanol and its hydrochloride, in the (±)-erythro form In a Parr reaction flask, 12 g (0.035 mol) of the previously obtained ketone are dissolved in 120 ml of methanol. 20 ml of acetic acid are added and the vessel is purged with nitrogen. 1.2 g of 10% palladium-on-charcoal are then introduced and hydrogenation is carried out at 50° C. for 6 hours under a pressure of about 0.35 Mpa. The catalyst is then poisoned with 50 ml of chloroform and filtered off and the filtrate is evaporated in vacuo in a water bath. The crystalline residue is taken up in water, ethyl acetate and aqueous ammonia solution. The organic phase is separated off, washed, dried and evaporated. The residue is taken up in 50 ml of diethyl ether and the mixture is stirred for 30 minutes in an ice bath. The white precipitate is filtered off and chromatographed on 50 g of silica using acetone as the eluant. 3.5 g of white crystals of the product in the form of the base are finally collected. To prepare the hydrochloride, the crystals are dissolved in 50 ml of absolute ethanol, 20 ml of ethanol saturated with hydrogen chloride are added, the mixture is stirred for 15 minutes, the ethanol is driven off on a rotary evaporator, the residue is taken up in 60 ml of anhydrous diethyl ether, the mixture is stirred for 15 minutes, the white precipitate is filtered off, washed with diethyl ether and dissolved in 200 ml of n-propanol, the solution is concentrated to 100 ml and the mixture is left overnight in the refrigerator. The white crystals obtained are then filtered off, washed with anhydrous diethyl ether and dried. They melt at 223°–225° C.

EXAMPLE 27

2-(4-Benzylpiperidino)-1-phenylpropanol and its hydrochloride 1. 2-(4-Benzylpiperidino)-propiophenone 17.5 g (0.1 mol) of 4-benzylpiperidine and then 12 g of sodium carbonate are added to a solution of 21.3 g (0.1 mol) of 2-bromopropiophenone in 100 ml of ethanol, and the mixture is heated under reflux for 2 hours. It is then filtered and the solvent is driven off. An oil remains, which is used as such in the subsequent reduction.

2. 2-(4-Benzylpiperidino)-1-phenylpropanol and its hydrochloride, in the (±)-erythro form 15 g (0.048 mol) of the previously obtained oil are dissolved in 150 ml of ethanol, 75 ml of acetic acid are added and 10 g of potassium borohydride are then added gradually while the mixture is being cooled, and the mixture is stirred for one hour at ambient temperature. 200 ml of ice and then 200 ml of methylene chloride are subsequently added and the mixture is rendered basic with aqueous ammonia solution. When washed, dried and evaporated, the organic phase produces a crystalline residue, which is washed with ethanol and then with petroleum ether. The hydrochloride is prepared by adding 80 ml of ethanol and then 20 ml of ethanol saturated with hydrogen chloride. The mixture is heated under reflux for 5 minutes, filtered hot and left to cool. The residue is filtered off, washed with a small amount of ethanol and dried. It sublimes at about 250 C. and decomposes at 259°–262° C.

EXAMPLE 28

2-(4-Benzylpiperidino)-1-(4-methylphenyl)-propanol and its hydrochloride 1. 2-(4-Benzylpiperidino)-4'-methylpropiophenone 20.5 g (0.09 mol) of 2-bromo-4'-methylpropiophenone are introduced into 100 ml of ethanol, 16 g (0.09 mol) of benzylpiperidine and then 12 g of sodium carbonate are added and the mixture is then heated under reflux for 2 hours. Thin layer chromatography shows that the reaction is complete. The mixture is filtered and the solvent is driven off. This gives an oil, which is used as such in the subsequent reduction.

2. 2-(4-Benzylpiperidino)-1-(4-methylphenyl)-propanol and its hydrochloride, in the (±)-erythro form 15 g (0.046 mol) of 2-(4-benzylpiperidino)-4'-methylpropiophenone are introduced into 150 ml of ethanol, and 75 ml of acetic acid are added. The vessel is immersed in an ice bath and 10 g of potassium borohydride are added slowly, with stirring. Stirring is then continued for one hour at ambient temperature. 400 ml of ice and then 200 ml of methylene chloride are then added and the mixture is rendered basic with concentrated aqueous ammonia solution. The organic solution is washed, dried and evaporated. A crystalline product forms, when washed with ethanol and then with petroleum ether and dried, melts at 118° C. (Koffler). The hydrochloride is prepared with a solution of hydrogen chloride in ethanol; it sublimes at about 250° C. and decomposes at 251°–254° C.

EXAMPLE 29

2[4-(4-Methoxybenzyl)-piperidino]-1-(4-chlorophenyl)-propanol and its hydrochloride 1. 2-[4-(4-Methoxybenzyl)-piperidino]-4'-chloropropiophenone 2.80 g (0.02 mol) of potassium carbonate are added to a solution of 5 g (0.02 mol) of 2-bromo-4'-chloropropiophenone and 4.15 g (0.02 mol) of 4-(4-methoxybenzyl)-piperidine in 60 ml of dry ethanol and the mixture is heated under reflux for 5 hours, with stirring, and then left to stand for 48 hours. It is left to cool and filtered, the filter cake being washed with alcohol, and the filtrate is evaporated. An orange oily residue remains, which is taken up in a mixture of water and diethyl ether. The organic phase is separated off and the aqueous phase is extracted a second time with diethyl ether. The organic phases are combined, dried and evaporated to give 7.45 g of an orange-yellow oily residue, which crystallises partially at ambient temperature and which is used as such in the subsequent reduction.

2. 2-[4-(4-Methoxybenzyl)-piperidino]-1-(4-chlorophenyl)-propanol and its hydrochoride, in the ($\pm$)-erythro form The reduction is carried out as in Example 26.2 using 7.45 g of the previously prepared ketone, 2.5 g of potassium borohydride, 50 ml of ethanol and 20 ml of acetic acid. The mixture is stirred first for half an hour in an ice bath and then for 3 hours at ambient temperature, water and then concentrated aqueous ammonia solution are added and the mixture is extracted twice with methylene chloride. The combined organic phases are washed, dried and evaporated and the residue is triturated with diethyl ether to give 5.5 g of crystals. 5.4 g of these are dissolved in 100 ml of methanol, 145 ml of a 0.1N solution of hydrogen chloride in isopropyl alcohol are added, the solution is evaporated and the residue is recrystallised from 200 ml of isopropyl alcohol. 4.25 g of crystals melting at 201°–202° C. are recovered.

EXAMPLE 30

2-[4-(4-Fluorobenzyl)-piperidino]-1-(4-chlorophenyl)-propanol and its hydrochloride 1. 2-[4-(4-Fluorobenzyl)-piperidino]-4'-chloropropiophenone A solution of 4.95 g of 4-(4-fluorobenzyl)-piperidine hydrochloride in the minimum amount of water is rendered alkaline with concentrated sodium hydroxide solution and the mixture is extracted 3 times with methylene chloride and ethyl acetate. After washing, drying and evaporation, the organic phases give 4.3 g of the base in the form of a colourless oil. This is dissolved in 60 ml of ethanol, 5 g of 2-bromo-4'-chloropropiophenone and 2.8 g of potassium carbonate are added and the mixture is heated under reflux for 5 hours, with stirring. It is left to stand overnight at ambient temperature, the inorganic salt is separated off, the alcohol phase is evaporated to dryness, the oily residue is taken up in diethyl ether, the organic phase obtained is dried and filtered and a solution of hydrogen chloride in diethyl ether is added. The hydrochloride precipitates in the form of a gum which is difficult to filter off. It is extracted with water, the acid aqueous phase is separated off and a solution of hydrogen chloride in diethyl ether is again added to the ether phase. This operation is repeated three times, the combined aqueous phases are then rendered alkaline with sodium hydroxide and the base is extracted with diethyl ether and then with ethyl acetate. When washed, dried and then evaporated, the combined organic phases produce 5.8 g of a yellowish oily residue, which is used as such in the subsequent reduction.

2. 2-[4-(4-Fluorobenzyl)-piperidino]-1-(4-chlorophenyl)-propanol and its hydrochloride, in the ($\pm$)-erythro form The procedure of Example 26.2 is employed using 5.8 g of the previously prepared ketone, 1.7 g of potassium borohydride, 160 ml of ethanol and 50 ml of acetic acid. This gives 4.55 g of the final compound in the form of the base, after trituration with diethyl ether. After recrystallisation from isopropyl alcohol and drying, the hydrochloride melts at 211°–213° C.

EXAMPLE 31

2-(4-Benzylpiperidino)-1-(3-chlorophenyl)-propanol and its hydrochloride 1. 2-(4-Benzylpiperidino)-3'-chloropropiophenone A solution of 26.48 g (0.107 mol) of 2-bromo-3'-chloropropiophenone in 70 ml of acetonitrile is placed in a 500 ml three-necked round-bottomed flask equipped with a pressure equalizing funnel, a calcium chloride drying tube and a magnetic stirrer, and 37.5 g (0.214 mol) of 4-benzylpiperidine are then added at ambient temperature over a period of about 20 minutes, without stirring. The mixture warms up; it is allowed to return to ambient temperature and, after 3 hours, 4-benzylpiperidine hydrobromide is crystallised by cooling the mixture on ice and triturating it. The crystals are filtered off and washed with acetonitrile (2 × 10 ml) and the filtrate is diluted with 200 ml of diethyl ether. Further 4-benzylpiperidine hydrobromide precipitates and is filtered off. 100 ml of 3N hydrochloric acid are added to the filtrate and the mixture is stirred. Three phases form. The two lower phases are collected, the upper phase is taken up in a few ml of water and the aqueous phase obtained is combined with the two phases previously separated off. Precipitation occurs. The mixture is cooled on ice, stirred and filtered on a glass frit and the first crop of precipitate is dried in a vacuum oven. The filtrate deposits a second precipitate, which is shown by thin layer chromatography to be the same product as the first crop. A total of 34.06 g of crystals of the hydrochloride, melting at between 189° and 198° C., is thus recovered, which is used as such in the subsequent reduction.

2. 2-(4-Benzylpiperidino)-1-(3-chlorophenyl)-propanol and its hydrochloride, in the ($\pm$)-erythro form 300 ml of absolute ethanol and 150 ml of acetic acid are added to 34.06 g (0.09 mol) of the hydrochloride of the previously obtained ketone. The mixture is cooled on ice and 20.5 g (0.38 mol) of potassium borohydride are added gradually, the temperature being kept below 20° C. The mixture is stirred for 2 hours at ambient temperature and cooled on an ice bath and 350 ml of water and then 220 ml of 27% aqueous ammonia solution and 400 ml of ethyl acetate are added. The crystals formed are filtered off and the organic phase is washed with water. The crystals are taken up in 100 ml of 27% aqueous ammonia solution, and 150 ml of chloroform are added. The crystals dissolve completely. The organic phase is separated off, washed with water and added to the ethyl acetate phase resulting from the filtration. The mixture of the two organic phases is dried and is evaporated in vacuo. 36.1 g of white crystals are collected. After recrystallisation from ethanol, 23.9 g of white crystals melting at 124°–126° C. are obtained.

They are dissolved in 200 ml of chloroform, and 150 ml of diethyl ether saturated with hydrogen chloride are added slowly at 0° C. After the addition, the mixture is stirred for a further half an hour and the precipitated hydrochloride is filtered off on a glass frit, washed with diethyl ether (2×100 ml) and dried in vacuo at 50° C. This gives 25.66 g of white crystals, which melt at 246°–247° C. after recrystallisation from ethanol.

EXAMPLE 32

2-(4-Benzylpiperidino)-1-(2-chlorophenyl)-propanol and its hydrochloride 1. 2-(4-Benzylpiperidino-2'-chloropropiophenone The procedure of Example 31.1 is used, starting from 26.29 g of 2-bromo-2'-chloropropiophenone in 70 ml of acetonitrile, and 37.23 g of 4-benzylpiperidine. After the 4-benzylpiperidine hydrobromide has been separated off, the addition of hydrochloric acid does not cause precipitation of the hydrochloride of the ketone formed.

The latter is extracted with methylene chloride and the organic phase obtained is treated with 100 ml of 25% aqueous ammonia solution in order to return to the base form. After washing, drying and evaporation, 32.3 g of a brown oil are obtained, which is used as such in a subsequent reduction.

2. 2-(4-Benzylpiperidino)-1-(2-chlorophenyl)-propanol and its hydrochloride, in the (±)-erythro form The procedure of Example 31.2 is used, starting from the 32.3 g of ketone in the form of the base, in 300 ml of ethanol and 150 ml of acetic acid, and 53.95 g of potassium borohydride. The final hydrochloride melts at 227°–229° C. after recrystallisation from ethanol.

EXAMPLE 33

2-(4-Benzylpiperidino)-1-(4-chlorophenyl)-ethanol and its hydrochloride 1. 2-(4-Benzylpiperidino)-4'-chloroacetophenone A mixture of 23.35 g (0.1 mol) of 2-bromo-4'-chloroacetophenone, 17.5 g (0.1 mol) of 4-benzylpiperidine and 13.8 g (0.1 mol) of potassium carbonate in 250 ml of anhydrous ethanol is heated under reflux for 3 hours and then left to stand overnight. The inorganic materials are filtered off and washed with ethanol and the filtrate is evaporated in vacuo. A brown oily residue remains, which is triturated with diethyl ether. A solid forms and is filtered off and then washed with diethyl ether. The filtrate is collected and the solid is triturated with a mixture of dilute sodium hydroxide solution and ethyl acetate. The organic phase is separated off, washed, dried and combined with the previously obtained diethyl ether filtrate. After evaporation of the mixture in vacuo, an oil remains, which crystallises on standing and is used as such.

2. 2-(4-Benzylpiperidino)-1-(4-chlorophenyl)-ethanol and its hydrochloride

The previously obtained oil is diluted with 250 ml of ethanol and 125 ml of acetic acid, and 12.5 g of potassium borohydride are added slowly, with cooling to between 10° and 15° C. After the addition, the mixture is stirred for a further 1 and a half hours with cooling and then for 1 hour at ambient temperature; it is then poured into 800 ml of water, and concentrated aqueous ammonia solution is added. Extraction is carried out twice with methylene chloride and the organic phases are combined, washed with water, dried and evaporated. 25.3 g of an orange solid remain, which is triturated with diethyl ether; this gives 14.4 g of a beige solid. The hydrochloride is prepared by heating this solid in 500 ml of methanol and by adding 435 ml of a 0.1N solution of hydrogen chloride in isopropyl alcohol. After cooling, evaporation in vacuo and recrystallisation from 250 ml of isopropyl alcohol, the hydrochloride melts at 190°–191° C.

EXAMPLE 34

2-(4-Benzylpiperidino)-1-(2-methylphenyl)-propanol and its hydrochloride 1. 2-(4-Benzylpiperidino)-2'-methylpropiophenone A mixture of 25 g of 2-bromo-2'-methylpropiophenone, 70 ml of dry acetonitrile, 30 g of potassium carbonate and 19 g of 4-benzylpiperidine is stirred for 4 hours at ambient temperature. It is filtered in order to separate off the inorganic residue, and the filtrate is diluted with 200 ml of diethyl ether, which causes precipitation of 4-benzylpiperidine hydrobromide. This is filtered off; the filtrate deposits a second crop of hydrobromide, which is also separated off. The filtrate is then acidified with 300 ml of 3N hydrochloric acid. The intermediate propiophenone hydrochloride is an oil which is insoluble in both phases. The acid aqueous phase is extracted twice with methylene chloride, the extract is washed with water, and aqueous ammonia solution is added. The mixture is stirred and left to separate, the organic phase is dried, filtered and treated with about 100 g of silica in order to retain the traces of 4-benzylpiperidine, the mixture is filtered and the filtrate is evaporated. 10.9 g of an oil are collected.

2. 2-(4-Benzylpiperidino)-1-(2-methylphenyl)-propanol and its hydrochloride, in the (±)-erythro form The previously obtained oil is diluted with 100 ml of ethanol and 20 ml of acetic acid, and 5 g of ground sodium borohydride are added over a period of half an hour, with stirring in an ice bath. After 4 hours, 200 ml of 3N hydrochloric acid are added gradually. A precipitate forms and is left to stand overnight at ambient temperature. The precipitate is filtered off, washed with water and recrystallised twice from isopropyl alcohol. 5.9 g of a product which melts at 243°–245° C. are isolated.

EXAMPLE 35

2-(4-Benzylpiperidino)-1-(4-hydroxy-3-methylphenyl)-propanol and its hydrochloride 1. 2-(4-Benzylpiperidino)-4'-hydroxy-3'-methylpropiophenone 12.15 g (0.05 mol) of 2-bromo-4'-hydroxy-3'-methylpropiophenone are dissolved in 25 ml of ethanol, 8.75 g (0.05 mol) of 4-benzylpiperidine diluted in 25 ml of ethanol, and then 5.4 g (0.05 mol) of sodium carbonate, are added and the mixture is heated under reflux for 1 and a half hours. The solvent is driven off and the residue is chromatographed on 100 g of silica using acetone as the eluant. This gives 18.4 g of a thick oil, which is used as such.

2. 2-(4-Benzylpiperidino)-1-(4-hydroxy-3-methylphenyl)-propiophenone and its hydrochloride, in the (±)-erythro form 8.6 g (0.025 mol) of the previously obtained oil are dissolved in 86 ml of ethanol, 43 ml of acetic acid are added and 14 g of potassium borohydride are then added in small portions. The mixture is left to react overnight and 375 ml of water and 25 ml of ethyl acetate are then added slowly. 45 ml of aqueous ammonia solution are added, the mixture is stirred and further ethyl acetate (2×100 ml) is added. The organic phase is decanted, washed with water and dried over sodium sulphate. It is evaporated to give 9 g of an oil, which is purified by chromatography on 500 g of silica using, as the eluant, firstly a 90/10 mixture of diisopropyl ether/methanol and then, after the impurities have passed through, a 50/50 mixture of diisopropyl ether/methanol. The oil obtained is dissolved in 40 ml of ethyl acetate, a turbidity caused by inorganic materials is eliminated by filtration and 40 ml of 1N aqueous hydrochloric acid are added. The mixture is stirred for one hour at ambient temperature, the precipitate is filtered off, washed with hydrochloric acid and then with 20 ml of ethyl acetate and the product is filtered off and dried. 3.8 g of the hydrochloride melting at 200°–201° C. are isolated.

EXAMPLE 36

2-[4-(4-Methylbenzyl)-piperidino]-1-(3,4-dimethoxyphenyl)-propanol and its hydrochloride 1. 2-[4-(4-Methylbenzyl)-piperidino]-3',4'-dimethoxypropiophenone 5.4 g (0.05 mol) of sodium carbonate are added to a mixture of 13.65 g (0.05 mol) of 2-bromo-3',4'-dimethoxypropiophenone and 9.46 g (0.05 mol) of 4-(4-methylbenzyl)-piperidine in 50 ml of ethanol and the mixture is heated under reflux for 3 hours. It is then evaporated to dryness and the residue is passed through a column of silica using acetone as the eluant. This gives an oil, which is used as such.

2. 2-[4-(4-Methylbenzyl)-piperidino]-1-(3,4-dimethoxyphenyl)-propanol and its hydrochloride, in the (±)-erythro form The oil obtained above is dissolved in 190 ml of ethanol, 95 ml of acetic acid are added, 19 g of potassium borohydride are then added in small portions and the mixture is left to react overnight at ambient temperature. 150 ml of ethyl acetate, 750 ml of water and 200 ml of concentrated aqueous ammonia solution are then added. The organic phase is separated off, the aqueous phase is extracted again with 100 ml of ethyl acetate and the combined organic phases are washed, dried and evaporated. The oily residue is dissolved in 80 ml of ethyl acetate, 50 ml of 1N aqueous hydrochloric acid are added and the precipitated hydrochloride is stirred for 1 hour, filtered off and recrystallised from 330 ml of ethanol containing 0.5% of concentrated hydrochloric acid. This finally gives 15 g of crystals which melt at 244°–245° C.

EXAMPLE 37

2-(4-Benzylpiperidino)-1-(3,4-dichlorophenyl)-propanol and its hydrochloride 1. 2-(4-Benzylpiperidino)-3',4'-dichloropropiophenone 15 g of 3',4'-dichloropropiophenone are placed in a round-bottomed flask with 100 ml of chloroform, a pinch of aluminium chloride is added and 3.7 ml of bromine diluted in 10 ml of chloroform are then added slowly. The mixture is stirred overnight at ambient temperature and filtered and the solvent is driven off from the filtrate. 100 ml of ethanol, 12.9 g of 4-benzylpiperidine and 10.2 g of potassium carbonate are added to the oil obtained. The mixture is heated under reflux for 2 hours and filtered, the solvent is driven off from the filtrate and 23.9 g of an oil are collected, which is used as such.

2. 2-(4-Benzylpiperidino)-1-(3,4-dichlorophenyl)-propanol and its hydrochloride, in the (±)-erythro form 250 ml of ethanol and 125 ml of acetic acid are added to the oil obtained above and 16 g of potassium borohydride are added over a period of 15 minutes. The mixture is stirred for one hour in an ice bath, 600 ml of iced water are then added and the mixture is rendered basic with aqueous ammonia solution. It is extracted with methylene chloride (3×200 ml), the organic phase is dried and the solvent is evaporated off. This gives 24.3 g of an oil, which is dissolved in 250 ml of ethanol; 10 ml of ethanol saturated with hydrogen chloride are added. The precipitate formed is filtered off and recrystallised from ethanol. The hydrochloride obtained melts at 226°–227° C. with decomposition.

EXAMPLE 38

2-(4-Benzylpiperidino)-1-(3,5-dimethylphenyl)-propanol and its hydrochloride 1. 2-(4-Benzylpiperidino)-3',5'-dimethylpropiophenone 21 g of 2-bromo-3',5'-dimethylpropiophenone are introduced into 50 ml of acetonitrile, the mixture is cooled to 0° C., 30.5 g of 4-benzylpiperidine are added and the mixture is stirred for 3 hours. It is diluted with 30 ml of diethyl ether, the precipitated hydrobromide is filtered off and 150 ml of diethyl ether are added to the filtrate, which produces a second crop of precipitate. This is filtered off and the filtrate is treated twice with 200 ml of 3N hydrochloric acid. The diethyl ether phase is separated off. The aqueous phase contains the hydrochloride of the propiophenone formed, as an emulsion. This aqueous phase is extracted with methylene chloride, the organic phase obtained is washed with water, dilute aqueous ammonia solution is added, the organic phase is decanted, washed with water, dried, filtered and treated with 100 g of silica, the mixture is filtered and the filtrate is evaporated. 14.4 g of an oil remain.

2. 2-(4-Benzylpiperidino)-1-(3,5-dimethylphenyl)-propanol and its hydrochloride, in the (±)-erythro form The oil obtained above is dissolved in 200 ml of ethanol, the solution is cooled in an ice bath, 40 ml of acetic acid are added and 6.5 g of sodium borohydride are then added in small portions. After stirring for a further 1 hour, the mixture is diluted with 3N hydrochloric acid and the precipitate is stirred overnight, filtered off and recrystallised twice from ethanol. 7.6 g of crystals melting at 262°–264° C. are recovered.

EXAMPLE 39

2-[4-(4-Fluorobenzyl)-piperidino]-1-(4-hydroxy-3,5-dimethylphenyl)-propanol and its hydrochloride 1. 2-[4-(4-Fluorobenzyl)-piperidino]-4'-hydroxy-3',5'-dimethylpropiophenone 2.12 g (0.02 mol) of sodium carbonate are added to a mixture of 5.14 g (0.02 mol) of 2-bromo-4'-hydroxy-3',5'-dimethylpropiophenone and 4 g (0.02 mol) of 4-(4- fluorobenzyl)-piperidine in 25 ml of ethanol and the mixture is heated under reflux for 3 hours. It is left to stand overnight and then purified by chromatography on a column of silica using acetone as the eluant. This give 6.6 g of a brown oil, which is used as such.

2. 2-[4-(4-Fluorobenzyl)-piperidino]-1-(4-hydroxy-3,5-dimethylphenyl)-propanol and its hydrochloride, in the (±)-erythro form 33 ml of acetic acid are added to a solution of the previously obtained oil in 66 m of ethanol, 6.6 g of potassium borohydride are then added in small portions and the mixture is left to react overnight at ambient temperature. 350 ml of water are then added and the mixture is rendered basic with aqueous ammonia solution and extracted with ethyl acetate. After washing, drying and evaporation of the organic phase, the oily residue is dissolved in 50 ml of ethyl acetate, 10 ml of 1N aqueous hydrochloric acid are added and the mixture is stirred for 48 hours. The precipitate is then filtered off, washed with a mixture of 10 ml of 1N hydrochloric acid and 30 ml of ethyl acetate and dried. 1.9 g of crystals melting at 220°–221° C. remain.

EXAMPLE 40

2-[4-(4-Methylbenzyl)-piperidino]-1-(4-methoxy-3,5-dimethylphenyl)-propanol and its hydrochloride 1. 2-[4-(4-Methylbenzyl)-piperidino]-4'-methoxy-3',5'-dimethylpropiophenone 5.9 g (0.022 mol) of 2-bromo-4'-methoxy-3',5'-dimethylpropiophenone are dissolved in 30 ml of ethanol, 4.2 g (0.022 mol) of 4-(4-methylbenzyl)-piperidine and then 2.12 g (0.02 mol) of sodium carbonate are added and the mixture is heated under reflux for 2 hours. It is left to cool, the inorganic precipitate is filtered off and the filtrate is evaporated. The residual oil is purified by chromatography on silica using acetone as the eluant. This gives 8 g of a product, which is used as such.

2. 2-[4-(Methylbenzyl)-piperidino]-1-(4-methoxy-3,5-dimethylphenyl)-propanol and its hydrochloride, in the (±)-erythro form The oil obtained above is dissolved in 80 ml of ethanol and 20 ml of acetic acid, 0.8 g of platinum oxide is added and hydrogenation is carried out in a Parr apparatus at 50° C. and under a pressure of 0.35 MPa for 3 hours. The catalyst is then filtered off, the solvent is driven off from the filtrate, the residual oil is taken up in water, 10 ml of ethyl acetate are added and the mixture is rendered basic with concentrated aqueous ammonia solution and stirred for 15 minutes. The precipitate is filtered off, washed with water and dissolved in 120 ml of hot ethanol, and 75 ml of 1N aqueous hydrochloric acid are added. The mixture is filtered hot and left to cool. The hydrochloride crystallises. It is separated off and recrystallised from 100 ml of a 3/1 mixture of ethanol/1N hydrochloric acid. After drying, 3.67 g of crystals which melt at 255°–257° C. remain.

EXAMPLE 41

2-(4-Benzylpiperidino)-1-(4-methoxyphenyl)-propanol 76.1 g of 2-(4-benzylpiperidino)-1-(4-hydroxyphenyl)-propanol and 12.65 g of sodium methoide in 1.5 liters of methanol are stirred for 6 hours under nitrogen, the mixture is evaporated to dryness and the sodium salt obtained is taken up in 1.5 liters of dimethylformamide. 14.74 g of dimethylsulphate are then added and the mixture is stirred for 12 hours and left to stand overnight. 2 liters of water are added, the mixture is filtered, the filtrate is extracted with diethyl ether, the organic phases are washed, dried and evaporated and the crude residue is purified by chromatography on 200 g of alumina using methylene chloride as the eluant. After washing with a small amount of diethyl ether and drying, 20 g of crystals which melt at 131°–132° C. remain.

EXAMPLE 42

2-(4-Benzylpiperdino)-1-(4-ethylphenyl)-propanol and its hydrochloride 1. 2-(4-Benzylpiperidino)-4'-ethylpropiophenone A mixture of 17.2 g of 2-bromo-4'-ethylpropiophenone, 12.5 g of 4-benzylpiperidine and 9.9 g of potassium carbonate in 250 ml of dry ethanol is heated under reflux for 4 hours, with stirring. The inorganic product is filtered off and washed with ethanol and the alcohol phase is concentrated in vacuo. The oily residue is taken up in diethyl ether and the mixture is extracted twice with dilute hydrochloric acid. After it has been rendered clearly alkaline with sodium hydroxide, the acid aqueous phase is then extracted three times with ethyl acetate. The organic phases are combined, washed with water until the washings are neutral, dried and evaporated in vauco. This give 19.15 g of an oily residue.

2. 2-(4-Benzylpiperidino)-1-(4-ethylphenyl)-propanol and its hydrochloride, in the (±) erythro form In a 2 liter conical flask, 19 g of the previously obtained oily ketone are dissolved in 500 ml of dry ethanol and 150 ml of acetic acid and the solution is cooled in an ice bath, with stirring. 6.1 g of potassium borohydride are added in small portions so as to keep the temperature below 10° C. Stirring is continued for half an hour with cooling and then for 2 hours at ambient temperature. 500 ml of water are then added and the mixture is left to stand overnight. The homogeneous phase is then rendered alkaline with 28% aqueous ammonia solution and extracted twice with methylene chloride. The organic phases are combined, washed, dried and evaporated. 18.5 g of a whitish solid remain. This is then dissolved in the minimum amount of hot methanol, 550 ml of a 0.1N solution of hydrogen chloride in isopropyl alcohol are added and the mixture is stirred, while being allowed to cool, until homogenisation is complete. The mixture is concentrated to dryness and a beige solid is collected, which is recrystallised from isopropyl alcohol. 12 g of the pure hydrochloride, which melts at 239°–240° C., are finally isolated.

EXAMPLE 43

2-[4-(4-Methylbenzyl)-piperidino]-1-(4-benzyloxyphenyl)-propanol and its hydrochloride 1. 2-[4-(4-Methylbenzyl)-piperidino]-4'-benzyloxypropiophenone 13.7 g (0.05 mol) of 2-chloro-4'-(4-benzyloxyphenyl)-propiophenone are added to a solution of 9.4 g (0.05 mol) of 4-(4-methylbenzyl)-piperidine in 50 ml of ethanol, 5.3 g (0.05 mol) of sodium carbonate are then added and the mixture is heated under reflux for 3 and a half hours and left to stand overnight. The inorganic precipitate is filtered off, the ethanol is evaporated off, the oily residue is taken up in acetone and the acetone is evaporated off. The residual oil is chromatographed on 80 g of silica using acetone as the eluant, and 21 g of an oil used as such in the subsequent reduction, are collected.

2. 2-[4-Methylbenzyl)-piperidino]-1-(4-benzyloxyphenyl)-propanol and its hydrochloride, in the (±)-erythro form The previously obtained oil is dissolved in 200 ml of ethanol, 100 ml of acetic acid are added and 10 g of potassium borohydride are then added in small portions, with stirring. 750 ml of water are then added, followed by 50 ml of ethyl acetate and then by 70 ml of concentrated aqueous ammonia solution, the mixture is stirred for half an hour, the precipitate is filtered off, washed with water and taken up in 700 ml of ethanol containing 5% of concentrated hydrochloric acid, the mixture is heated under reflux and the solution obtained is filtered and left to cool, which causes precipitation of the hydrochloride. This is filtered off and dried. 13.3 g of white crystals melting at 221°–223° C. are thus isolated.

EXAMPLE 44

2-(4-Benzylpiperidino)-1-(4-benzoyloxyphenyl)-propanol 1. 2-(4-Benzylpiperidino)-4'-hydroxypropiophenone 25 g of 2-(4-benzylpiperidino)-4'-benzyloxypropiophenone are debenzylated in 200 ml of ethanol and 10 ml of acetic acid, in a Parr apparatus, in the presence of 1 g of 10% palladium-on-charcoal under a pressure of 0.1 MPa for 3 hours. The product obtained is isolated by filtering off the catalyst and evaporating off the solvent.

2. 2-(4-Benzylpiperidino)-4'-benzoyloxypropiophenone 2.36 ml of benzoyl chloride are added to 15 ml of pyridine containing 6 g of the previously obtained product, and the precipiate formed is stirred for 3 hours, diluted with diethyl ether, filtered off, rinsed with diethyl ether, dried, washed three times with water and dried. 6.8 g of the product are collected.

3. 2-(4-Benzylpiperidino)-1-(4-benzoyloxyphenyl)-propanol in the (±)-erythro form 6.7 g of the previously obtained product are stirred in 120 ml of ethanol and 25 ml of acetic acid in an ice bath, 3 g of sodium borohydride are added in small portions and the mixture is stirred for 2 hours. It is diluted with water, rendered basic with 7% aqueous ammonia solution and extracted with methylene chloride and the combined organic phases are washed, dried and evaporated. The solid obtained is triturated with diethyl ether and recrystallised from ethanol. After drying, 4 g of crystals melting at 152°–154° C. remain.

EXAMPLE 45

2-(4-Benzylpiperidino)-1-(4-palmitoyloxyphenyl)-propanol 1. 2-(4-Benzylpiperidino)-4'-palmitoyloxypropiophenone 6.5 g of palmitoyl chloride are added to 40 ml of pyridine containing 7 g of 2-(4-benzylpiperidino)-4'-hydroxypropiophenone and the mixture is stirred for 5 hours. It is diluted with 100 ml of diethyl ether and left to stand overnight. The precipitate is then collected by filtration, washed and dried. 11 g of a product which melts at 185°–192° C. with decomposition are thus isolated.

2. 2-(4-Benzylpiperidino)-1-(4-palmitoyloxyphenyl)-propanol in the (±)-erythro form 10 g of the previously obtained palmitate are suspended in 200 ml of ethanol and 20 ml of acetic acid, the suspension is stirred, the mixture is cooled in an ice bath, 5 g of sodium borohydride are added in small portions and the mixture is stirred for 5 hours and left to stand overnight at ambient temperature. The product is filtered off and stirred in a mixture of water, ethyl acetate and aqueous ammonia solution, the mixture is left to separate, the organic phase is washed, dried and evaporated and the white solid obtained is triturated with diisopropyl ether, filtered off, recrystallised from ethyl acetate and dried. 5.7 g of a product which melts at 75°–77° C. are isolated.

EXAMPLE 46

2-(4-Benzylpiperidino)-1-(4-hydroxy-3-hydroxymethylphenyl)-propanol and its neutral fumarate 1. 4'-Benzyloxy-3'-methoxycarbonylpropiophenone 38 g of potassium carbonate and 12.65 ml, (14 g) of benzyl chloride are added to 20.8 g of 4'-hydroxy-3'-methoxycarbonylpropiophenone in 100 ml of dimethylformamide. The mixture is heated at 60° C. for 4 hours, with stirring. It is then poured into iced water, the mixture is extracted with ethyl acetate and the organic phase is washed with water, dried and evaporated to dryness. The residual oil crystallises on trituration with pentane. The crystals are filtered off and recrystallised from ethanol. 18 g of crystals melting at 76°–78° C. are collected.

2. 2-(4-Benzyloxy-3-methoxycarbonylphenyl)-2-ethyl-1,3-dioxolane

A mixture of 15 g of the propiophenone prepared above, 6.4 ml of ethylene glycol and 1 g of p-toluenesulphonic acid in 200 ml of toluene is heated under reflux for 10 hours. The toluene phase is then washed with 500 ml of a 5% solution of sodium carbonate and then with water, dried over sodium sulphate and evaporated to dryness. The residual oil is chromatographed on alumina using toluene as the eluant. 11 g of purified oil are isolated.

3. 2-(4-Benzyloxy-3-hydroxymethylphenyl)-2-ethyl-1,3-dioxolane

A solution of 11 g of the previously prepared dioxolane in 75 ml of diethyl ether is added dropwise, at ambient temperature, to a suspension of 1.2 g of lithium aluminium hydride in 75 ml of diethyl ether and the mixture is then heated under reflux for one hour. The excess hydride is destroyed by adding 2.2 ml of water and 1.2 ml of 2.5N sodium hydroxide solution, the insoluble material is filtered off and the diethyl ether phase is dried over sodium sulphate and evaporated to dryness. 9.2 g of an oil are collected, which is purified on alumina using an 80/20 mixture of toluene/chloroform as the eluant.

4. 4'-Benzyloxy-3'-hydroxymethylpropiophenone

A mixture of 9 g of the dioxolane prepared as indicated above and 150 ml of 3N hydrochloric acid is heated at 60° C. for half an hour. It is left to cool and extracted with ethyl acetate and the organic phase is washed, dried and evaporated. After recrystallization of the residue from benzene, 6 g of crystals melting at 95°–96° C. remain.

5. 2-Bromo-4'-benzyloxy-3'-hydroxymethylpropiophenone 200 ml of tetrahydrofuran and 6 g of the previously prepared propiophenone are placed in a 500 ml conical flask. 2.07 g (1.84 ml) of pyrrolidinone and 12.05 g of pyrrolidinone hydrotribromide are added and the mixture is heated under reflux for one hour. A whitish precipitate forms and is filtered off, the filtrate is evaporated to dryness, the residual oil is taken up in chloroform and the organic phase thus obtained is washed, dried and evaporated and the residue crystallized from a mixture of toluene and pentane. 7 g of a product which melts at 80° C. are thus isolated.

6. 2-(4-Benzylpiperidino)-4'-benzyloxy-3'-hydroxymethylpropiophenone

A mixture of 7 g of the brominated propiophenone and 7 g of 4-benzylpiperidine in 200 ml of acetonitrile is heated under reflux for 3 hours and cooled and 500 ml of diethyl ether are added. Benzylpiperidine hydrobromide precipitates and is filtered off, the filtrate is evaporated to dryness, the oily residue is taken up in 4N hydrochloric acid and the mixture is extracted with diethyl ether. The hydrochloride comes down in the form of a third oily phase. Three extractions are carried out with 200 ml of diethyl ether. The ether phase is drawn off under reduced pressure, the operation is repeated three times with 200 ml of diethyl ether, the residual oil is then extracted with chloroform and the chloroform phase is decanted, washed with water, dried and evaporated to dryness. 9 g of the hydrochloride are collected.

7. 2-(4-Benzylpiperidino)-1-(3-hydroxymethylphenyl)-propanol and its neutral fumarate, in the ($\pm$)-erythro form A mixture of 200 ml of methanol and 50 ml of acetic acid containing 19 g of the above propiophenone is subjected to hydrogenation for 4 hours on palladium-on-charcoal at 40° C. under a pressure of 0.28 MPa, in a Parr apparatus. The catalyst is then regenerated and the hydrogenation is repeated at 40° C. The catalyst is filtered off, the filtrate is concentrated to dryness, the residue is taken up in 3N aqueous ammonia solution and the mixture is extracted with ethyl acetate. The organic phase is washed, dried and evaporated and the residual oil is chromatographed on silica using a 90/10 mixture of chloroform/methanol as the eluant. This gives 3 g of product; its neutral fumarate is prepared by adding the stoichiometric amount of anhydrous fumaric acid. The fumarate is isolated by filtration and recrystallized from ethanol. 2.0 g of the product, which melts at 208°–210° C., are obtained.

EXAMPLE 47

2-(4-Benzylpiperidino)-1-(4-hydroxy-3-methoxycarbonylphenyl)-propanol and its hydrochloride 1. 2-(4-Benzylpiperidino)-4'-hydroxy-3'-methoxycarbonyl-propiophenone 300 ml of methyl ethyl ketone containing 57.4 g of 2-bromo-4'-hydroxy-3'-methoxycarbonylpropiophenone, 35 g of 4-benzylpiperidine and 30.6 g of potassium carbonate are heated under reflux for 4 hours. The precipitate is filtered off hot, the filtrate is evaporated to dryness, the residue is taken up in 3N hydrochloric acid and the mixture is extracted with diethyl ether. The ether phase is stirred for one hour; the hydrochloride crystallizes and is filtered off, rinsed with diethyl ether and transferred to a beaker containing water rendered alkaline with 3N aqueous ammonia solution, and the base freed in this way is extracted with ethyl acetate. After washing, drying and evaporation of the organic phase, 52 g of product are obtained, which is used as such.

2. 2-(4-Benzylpiperidino)-1-(4-hydroxy-3-methoxycarbonylphenyl)-propanol and its hydrochloride, in the ($\pm$)-erythro form 47.6 g of the above propiophenone are placed in a 2 liter conical flask together with 500 ml of methanol and 250 ml of acetic acid. The mixture is cooled in ice and 50 g of potassium borohydride are added in small portions. The mixture is stirred for 3 hours and then left to stand overnight. Iced water is added and the mixture is rendered alkaline with 3N aqueous ammonia solution and extracted with ethyl acetate. The organic phase is washed, a precipitate is filtered off and set aside, the organic phase is decanted, dried and evaporated, the residue is dissolved in methanol, an excess of a 2.9N solution of hydrogen chloride in diethyl ether is added and the hydrochloride which precipitates is separated off and dried. The hydrochloride is prepared in the same manner from the precipitate previously set aside. The two crops of hydrochloride are combined and recrystallized from methanol. This gives 25 g of crystals which melt at 228°–230° C.

EXAMPLE 48

2-(4-Benzylpiperidino)-1-(4-hydroxy-3-carbamoylphenyl)-propanol and its hydrochloride A solution of 7 g of 2-(4-benzylpiperidino)-1-(4-hydroxy-3-methoxycarbonylphenyl)-propanol hydrochloride in 200 ml of methanol is placed in a pressure bottle, an approximately 0.2 g piece of sodium is added and ammonia gas is bubbled in up to saturation. The mixture is stirred for 4 days and then evaporated to dryness. The residue is taken up in isopropyl alcohol, a solution of hydrogen chloride in propanol is added and the hydrochloride is recrystallized from ethanol. 3.8 g of the product, which melts at 215°–217° C., are isolated.

EXAMPLE 49

2-[4-(4-Fluorobenzyl)-piperidino]-1-(4-chlorophenyl)-ethanol and its hydrochloride 1. 2-[4-(4-Fluorobenzyl)-piperidino]-4'-chloroacetophenone 78 ml of ethanol are placed in a 250 ml conical flask and 2 ml of a 5.3N methanolic solution of sodium methoxide are added. 2.29 g (0.01 mol) of 4-(4-fluorobenzyl)-piperidine hydrochloride are added and the mixture is stirred for 15 minutes. 1.38 g of potassium carbonate are then added, followed by 2.33 g (0.01 mol) of 2-bromo-4'-chloroacetophenone, and the mixture is heated under reflux for 2 hours. It is left to cool, the inorganic precipitate is filtered off, the filtrate is evaporated to dryness and the residual oil is taken up in 1N hydrochloric acid. Extraction is carried out with chloroform and the organic phase is washed with water, dried over sodium sulphate and evaporated to dryness. 3.22 g of the crude hydrochloride remain in the form of an oil, which is used as such but which can be recrystallized from a mixture of acetone/diethyl ether (melting point=168° C.).

2. 2-[4-(4-Fluorobenzyl)-piperidino]-1-(4-chlorophenyl)-ethanol and its hydrochloride A solution of 3.22 g of the previously obtained oil in 100 ml of methanol is placed in a 250 ml conical flask. The solution is cooled in a mixture of ice and water, 1.13 g of potassium borohydride are added in small amounts and stirring is continued for 8 hours at ambient temperature. The mixture is then rendered alkaline with 3N aqueous ammonia solution, extraction is carried out with ethyl acetate and the extracts are washed with water, dried and evaporated to dryness. The residue is recrystallized from isopropyl alcohol, filtered off and washed with pentane. The base obtained melts at 126°–127° C.

The hydrochloride is prepared by dissolving the base in acetone and adding a stoichiometric amount of a solution of hydrogen chloride in diethyl ether. The hydrochloride precipitates. It is filtered off and recrystallized first from isopropyl alcohol and then from a mixture of diethyl ether/ethanol. After drying, it melts at 218°–220° C.

TABLE

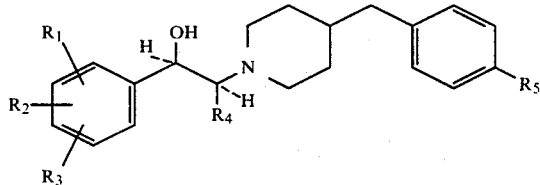 (I)

(±)-erythro (except for compounds Nos. 7, 12, 61 and 63 to 82)

| No. | Example | R₁ | R₂ | R₃ | R₄ | R₅ | Salt/base | Melting point (°C.) |
|---|---|---|---|---|---|---|---|---|
| 1 | 28 | 4-CH₃ | H | H | CH₃ | H | HCl | 251–254 (d) |
| 2 | 27 | H | H | H | CH₃ | H | HCl | 259–262 (d) |
| 3 | 41 | 4-OCH₃ | H | H | CH₃ | H | Base | 131–132 |
| 4 | 26 | 4-OH | H | H | CH₃ | CH₃ | HCl | 223–225 |
| 5 |  | H | H | H | CH₃ | CH₃ | HCl | 239–241 |
| 6 | 43 | 4-OCH₂—C₆H₅ | H | H | CH₃ | CH₃ | HCl | 221–223 |
| 7 | 33 | 4-Cl | H | H | H | H | HCl | 190–191 |
| 8 |  | 4-Cl | H | H | CH₃ | CH₃ | HCl | 234–235 |
| 9 | 29 | 4-Cl | H | H | CH₃ | OCH₃ | HCl | 201–202 |
| 10 |  | 4-F | H | H | CH₃ | CH₃ | HCl | 241–242 |
| 11 | 30 | 4-Cl | H | H | CH₃ | F | HCl | 211–213 |
| 12 |  | 4-F | H | H | H | H | HCl | 200–201 |
| 13 | 44 | 4-OCO—C₆H₅ | H | H | CH₃ | H | Base | 152–154 |
| 14 | 45 | 4-OCOC₁₅H₃₁ | H | H | CH₃ | H | Base | 75–77 |
| 15 |  | 3-CH₃ | H | H | CH₃ | H | HCl | 246–249 |
| 16 | 34 | 2-CH₃ | H | H | CH₃ | H | HCl | 243–245 |
| 17 |  | 3-Br | H | H | CH₃ | H | HCl | 229–230 |
| 18 |  | 4-CF₃ | H | H | CH₃ | H | HCl | 218–219 |
| 19 |  | 3-CF₃ | H | H | CH₃ | H | HCl | 254–256 |
| 20 | 31 | 3-Cl | H | H | CH₃ | H | HCl | 246–247 |
| 21 |  | 3-F | H | H | CH₃ | H | HCl | 257–259 |
| 22 |  | 2-CF₃ | H | H | CH₃ | H | HCl | 206–208 |
| 23 | 42 | 4-C₂H₅ | H | H | CH₃ | H | HCl | 239–240 |
| 24 |  | 4-C₂H₅ | H | H | CH₃ | F | HCl | 242–243 |
| 25 |  | 3-OH | H | H | CH₃ | H | HCl | 212–214 |
| 26 |  | 3-OCH₂—C₆H₅ | H | H | CH₃ | H | HCl | 219–221 |
| 27 |  | 2-F | H | H | CH₃ | H | HCl | 220–222 |
| 28 | 32 | 2-Cl | H | H | CH₃ | H | HCl | 227–229 |
| 29 |  | 3-OH | H | H | CH₃ | CH₃ | HCl | 206–207 |
| 30 | 37 | 3-Cl | 4-Cl | H | CH₃ | H | HCl | 226–227 (d) |
| 31 |  | 3-COOC₂H₅ | 4-OH | H | CH₃ | H | HCl | 236–238 |
| 32 | 47 | 3-COOCH₃ | 4-OH | H | CH₃ | H | HCl | 228–230 |
| 33 | 38 | 3-CH₃ | 5-CH₃ | H | CH₃ | H | HCl | 262–264 |
| 34 | 48 | 3-CONH₂ | 4-OH | H | CH₃ | H | HCl | 215–217 |
| 35 |  | 2-Cl | 4-Cl | H | CH₃ | H | HCl | >260 (s) |
| 36 | 35 | 3-CH₃ | 4-OH | H | CH₃ | H | HCl | 200–201 |
| 37 |  | 3-CH₃ | 4-OCH₃ | H | CH₃ | H | HCl | 232–234 |
| 38 |  | 3-OCH₃ | 4-OCH₃ | H | CH₃ | H | HCl | 241–242 |
| 39 | 36 | 3-OCH₃ | 4-OCH₃ | H | CH₃ | CH₃ | HCl | 244–245 |
| 40 |  | 3-F | 4-OH | H | CH₃ | H | HCl | 218–220 |

TABLE-continued

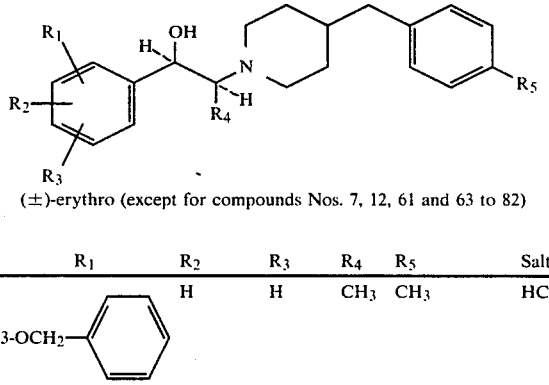

(±)-erythro (except for compounds Nos. 7, 12, 61 and 63 to 82)

| No. | Example | $R_1$ | $R_2$ | $R_3$ | $R_4$ | $R_5$ | Salt/base | Melting point (°C.) |
|---|---|---|---|---|---|---|---|---|
| 41 | | 3-OCH$_2$-phenyl | H | H | CH$_3$ | CH$_3$ | HCl | 217–219 |
| 42 | | 3-CF$_3$ | H | H | CH$_3$ | F | HCl | 254–256 (s) |
| 43 | | 3-Cl | 4-OH | H | CH$_3$ | H | HCl | 218–220 |
| 44 | | 3-COOCH$_3$ | 4-OCH$_3$ | H | CH$_3$ | H | HCl | 250 (d) |
| 45 | | 3-Cl | 4-OCH$_3$ | H | CH$_3$ | CH$_3$ | HCl | 220–222 |
| 46 | 46 | 3-CH$_2$OH | 4-OH | H | CH$_3$ | H | Fum. | 208–210 |
| 47 | | 3-F | 4-OCH$_3$ | H | CH$_3$ | H | HCl | 198–200 |
| 48 | | 3-Cl | 4-OCH$_3$ | H | CH$_3$ | H | HCl | 228–230 |
| 49 | | 3-Cl | 5-Cl | H | CH$_3$ | H | HCl | 260–268 |
| 50 | | 3-CH$_3$ | 4-OH | 5-CH$_3$ | CH$_3$ | CH$_3$ | HCl | 237–239 |
| 51 | 40 | 3-CH$_3$ | 4-OCH$_3$ | 5-CH$_3$ | CH$_3$ | CH$_3$ | HCl | 255–257 |
| 52 | | 3-CH$_3$ | 4-OH | 5-CH$_3$ | CH$_3$ | H | HCl | 199–201 |
| 53 | 39 | 3-CH$_3$ | 4-OH | 5-CH$_3$ | CH$_3$ | F | HCl | 220–221 |
| 54 | | 4-CH$_3$ | H | H | CH$_3$ | CH$_3$ | HCl | 241–242 |
| 55 | | 4-CH$_3$ | H | H | CH$_3$ | F | HCl | 234–235 |
| 56 | | 4-OCH$_3$ | H | H | CH$_3$ | CH$_3$ | HCl | 225–227 |
| 57 | | 2-Cl | 4-Cl | H | CH$_3$ | F | HCl | 220–222 |
| 58 | | 4-Cl | H | H | CH$_3$ | 3,4,5-(OCH$_3$) | HCl | 165–166 (d) |
| 59 | | 3-F | 4-OCH$_3$ | H | CH$_3$ | F | HCl | 221–213 |
| 60 | | 3-Cl | 4-OCH$_3$ | H | CH$_3$ | F | HCl | 234–236 |
| 61 | 49 | 4-Cl | H | H | H | F | HCl | 218–220 |
| 62 | | 3-OCH$_3$ | H | H | CH$_3$ | H | HCl | 228–230 |
| 63 | | 4-Br | H | H | H | H | HCl | 204–205 |
| 64 | | 3-Cl | 4-Cl | H | H | H | HCl | 214–215 |
| 65 | | 2-Cl | H | H | H | H | HCl | 218–220 |
| 66 | | 3-Cl | H | H | H | H | HCl | 215–216 |
| 67 | | 3-Cl | H | H | H | F | HCl | 245–246 |
| 68 | | 4-F | H | H | H | F | HCl | 213–215 |
| 69 | | 2-Cl | H | H | H | F | HCl | 182 |
| 70 | | 3-Cl | 4-Cl | H | H | F | HCl | 236–238 |
| 71 | | 2-Br | H | H | H | F | HCl | 202–204 |
| 72 | | 3-Br | H | H | H | F | HCl | 247–248 |
| 73 | | 4-Br | H | H | H | F | HCl | 214 |
| 74 | | H | H | H | H | F | HCl | 235 |
| 75 | | 4-OH | H | H | H | F | HCl | 193–194 |
| 76 | | 4-CF$_3$ | H | H | H | F | HCl | 208–210 |
| 77 | | 2-CH$_3$ | H | H | H | F | HCl | 206–207 |
| 78 | | 3-CH$_3$ | H | H | H | F | HCl | 208–209 |
| 79 | | 4-CH$_3$ | H | H | H | F | HCl | 209–210 |
| 80 | | 2-OCH$_3$ | H | H | H | F | HCl | 222–224 |
| 81 | | 3-OCH$_3$ | H | H | H | F | HCl | 202–204 |
| 82 | | 4-OCH$_3$ | H | H | H | F | HCl | 159–160 |
| 83 | | 2-Cl | H | H | Et | H | HCl | 217–218 |
| 84 | | 4-Cl | H | H | Et | H | HCl | 214–215 |

Key:
(d): decomposition
(s): sublimation
HCl: hydrochloride
Fum: fumarate

The compounds of the invention were subjected to pharmacological tests.

The toxicity (50% lethal dose LD$_{50}$) of the compounds was determined on mice of the CD1 strain by a graphical method.

The LD$_{50}$ values range from 30 to 1000 mg/kg, administered intraperitoneally, and from 100 to more than 1000 mg/kg, administered orally.

The compounds of the invention were subjected to the complete cerebral ischaemia test in mice. The ischaemia is due to a cardiac arrest induced by a rapid intravenous injection of MgCl$_2$. In this test, the "survival time" is measured, that is to say the period of time between the injection of MgCl$_2$ and the last observable respiratory movement of each mouse. This last movement is considered as the final indication of function of the central nervous system.

The respiratory arrest occurs approximately 19 seconds after the injection of MgCl$_2$.

Male mice (CD1 Charles River) are studied in groups of 10.

The mice are given an unlimited supply of food and water before the tests. The survival time is measured 10 minutes after the intraperitoneal administration of the compounds of the invention in a liquid vehicle. The results are given in the form of the difference between the survival time measured on a group of 10 mice which have received the compound and the survival time measured on a control group of 10 mice which have received the liquid vehicle.

The ratios of the changes in the survival time to the dose of the compound are recorded graphically according to a semilogarithmic curve.

This curve makes it possible to calculate the 3 second effective dose ($ED_{3''}$), that is to say the dose (in mg/kg) which prolongs the survival time by 3 seconds compared with the control group of 10 untreated mice.

An increase of 3 seconds in the survival time is both statistically significant and reproducible.

The $ED_{3''}$ values of the compounds of the invention range from 5 to 100 mg/kg, administered intraperitoneally.

The pharmacological study of the compounds of the invention shows that they possess an antianoxic activity and that they can be used in therapy for the treatment of vigilance disorders, in particular for combating the behavioural disorders attributable to cerebral vascular damage and to the cerebral sclerosis encountered in geriatrics, and also for the treatment of metabolic encephalopathies and for the treatment of depressive states.

The invention consequently includes all pharmaceutical compositions containing the compounds and/or their salts as active principles, in association with any excipients which are suitable for their administration, in particular their oral or parenteral administration.

The invention accordingly provides pharmaceutical compositions which comprise, as active ingredient, at least one compound of general formula I, or a pharmaceutically acceptable acid addition salt thereof, in association with a pharmaceutically acceptable carrier.

The compounds can be administered orally or parenterally.

The daily dosage can range from 1 to 100 mg, administered parenterally, and from 5 to 500 mg, administered orally.

We claim:

1. The compound 2-[4-(4-fluorobenzyl)-piperidino]-1-(4-chlorophenyl)-ethanol or a pharmaceutically acceptable acid addition salt thereof.

2. A method for treating a subject suffering from anoxia, comprising administering to said subject an amount of a compound according to claim 1 effective for the treatment of anoxia.

3. A pharmaceutical composition which comprises, as active ingredient, an effective amount of a compound as claimed in claim 1, or a pharmaceutically acceptable acid addition salt thereof, in association with a pharmaceutically acceptable carrier.

* * * * *